(12) United States Patent
Bernstein

(10) Patent No.: US 10,758,313 B2
(45) Date of Patent: Sep. 1, 2020

(54) CONTROLLING ROLL FOR A DEVICE IN A COMPUTER-ASSISTED MEDICAL SYSTEM

(71) Applicant: Intuitive Surgical Operations, Inc., Sunnyvale, CA (US)

(72) Inventor: Nicholas Bernstein, Cary, NC (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 330 days.

(21) Appl. No.: 15/766,778

(22) PCT Filed: Oct. 4, 2016

(86) PCT No.: PCT/US2016/055356
§ 371 (c)(1),
(2) Date: Apr. 6, 2018

(87) PCT Pub. No.: WO2017/062370
PCT Pub. Date: Apr. 13, 2017

(65) Prior Publication Data
US 2018/0280105 A1    Oct. 4, 2018

Related U.S. Application Data

(60) Provisional application No. 62/238,549, filed on Oct. 7, 2015.

(51) Int. Cl.
*A61B 90/11* (2016.01)
*A61B 17/34* (2006.01)
(Continued)

(52) U.S. Cl.
CPC .......... *A61B 90/11* (2016.02); *A61B 17/3421* (2013.01); *A61B 34/37* (2016.02); *B25J 9/1689* (2013.01); *G05B 19/402* (2013.01)

(58) Field of Classification Search
None
See application file for complete search history.

(56) References Cited

U.S. PATENT DOCUMENTS

| 5,590,034 A | 12/1996 | Snell |
| 2006/0074406 A1 | 4/2006 | Cooper et al. |

(Continued)

FOREIGN PATENT DOCUMENTS

EP    2671689 A1    12/2013

OTHER PUBLICATIONS

International Preliminary Report on Patentability for Application No. PCT/US2016/055359, dated Apr. 19, 2018, 8 pages.

(Continued)

*Primary Examiner* — Bhavesh V Amin
(74) *Attorney, Agent, or Firm* — Ferguson Braswell Fraser Kubasta PC

(57) ABSTRACT

Roll control is provided for a device by controlling the roll-angle offset about the device roll axis in correspondence to a specified rotation of a reference frame for the device. This specified rotation may correspond to a roll-free rotation of the reference frame to align a corresponding reference roll axis with the device roll axis. In applications to robotics generally, the device may be characterized as a robotic element or a robotically-supported instrument. In specific applications to robotic surgery in a computer-assisted medical system, the device may include a spar or cannula that is configured to support a surgical instrument.

20 Claims, 24 Drawing Sheets

(51) Int. Cl.
    *A61B 34/37*    (2016.01)
    *B25J 9/16*     (2006.01)
    *G05B 19/402*   (2006.01)

(56) References Cited

U.S. PATENT DOCUMENTS

| 2011/0046925 A1 | 2/2011  | Bidard et al.   |
| 2013/0325031 A1 | 12/2013 | Schena et al.   |
| 2013/0325032 A1 | 12/2013 | Schena et al.   |
| 2014/0277738 A1 | 9/2014  | Diolaiti et al. |

OTHER PUBLICATIONS

International Search Report and Written Opinion for Application No. PCT/US2016/055356, dated Jan. 17, 2017, 11 pages.
International Search Report and Written Opinion for Application No. PCT/US2016/055359, dated Jan. 13, 2017, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

CONTROLLING ROLL FOR A DEVICE IN A COMPUTER-ASSISTED MEDICAL SYSTEM

RELATED APPLICATIONS

This patent application is a U.S. National Stage Filing under 35 U.S.C. 371 from International Application No. PCT/US2016/055356, filed on Oct. 4, 2016, and published as WO 2017/062370 A1 on Apr. 13, 2017, which claims priority to and the benefit of the filing date of U.S. Provisional Patent Application 62/238,549, entitled "CONTROLLING ROLL FOR A DEVICE IN A COMPUTER-ASSISTED MEDICAL SYSTEM" filed Oct. 7, 2015, each of which is incorporated by reference in its entirety.

BACKGROUND

This disclosure relates generally to robotic control and particularly to control for surgical robotic systems.

Minimally invasive surgical techniques are aimed at reducing the amount of extraneous tissue that is damaged during surgical procedures in order to minimize patient discomfort, recovery time, and harmful side effects.

SUMMARY

Certain embodiments provide roll control for a device by rotating the device about a given roll axis so that the angular displacement corresponds to a reference orientation for the device. In applications to robotics generally, the device may be characterized as a robotic element or a robotically-supported instrument. In specific applications to robotic surgery in a computer-assisted medical system, the device may include a spar or cannula that is configured to support a surgical instrument.

One embodiment relates to a method for controlling roll for a device. A first operation includes specifying a reference frame that corresponds to a reference orientation for the device, the reference frame including a reference pitch axis, a reference yaw axis and a reference roll axis. A second operation includes accessing values for a device frame that corresponds to an orientation of the device, the device frame including a device pitch axis, a device yaw axis, and a device roll axis. A third operation includes determining a roll-angle offset that characterizes an angular difference about the device roll axis between the device frame and a roll-axis-alignment rotation of the reference frame, the roll-axis-alignment rotation corresponding to a rotation about a combination of the reference pitch axis and the reference yaw axis to align the reference roll axis with the device roll axis. A fourth operation includes controlling roll for the device by controlling the roll-angle offset about the device roll axis. For example, controlling the roll-angle offset may include rotating the device about the device roll axis to maintain a specified roll-angle offset (e.g., zero or less than a specified tolerance). Alternatively more complex adjustments in the roll-angle offset can be made dynamically including smooth transitions from one set point to another.

Another embodiment relates to a method that includes operations based on pitch and yaw inputs for controlling a device. A first operation includes accessing values for a device frame that corresponds to an orientation of the device, the device frame including a device yaw axis, a device pitch axis, and a device roll axis. A second operation includes specifying a reference frame from the accessed values of the device frame at a reference-specifying time, the reference frame corresponding to a reference orientation for the device, and the reference frame including a reference yaw axis, a reference pitch axis, and a reference roll axis. A third operation includes accessing values for a yaw-pitch combination that includes at least one rotation about the device yaw axis and at least one rotation about the device pitch axis. A fourth operation includes controlling the device from an initial device state by implementing the pitch-yaw combination with a roll-control operation for controlling a roll-angle offset about the device roll axis, the roll-angle offset characterizing an angular difference about the device roll axis between the device frame and a roll-axis-alignment rotation of the reference frame, and the roll-axis-alignment rotation corresponding to a rotation about a combination of the reference yaw axis and the reference pitch axis to align the reference roll axis with the device roll axis.

Another embodiment relates to an apparatus for carrying out any one of the above-described methods, where the apparatus includes a computer for executing instructions related to the method. For example, the computer may include a processor for executing at least some of the instructions. Additionally or alternatively the computer may include circuitry or other specialized hardware for executing at least some of the instructions. In some operational settings, the apparatus may be configured as a system that includes one or more units, each of which is configured to carry out some aspects of the method either in software, in hardware or in some combination thereof. At least some values for the results of the method can be saved for later use in a computer-readable medium, including memory units and storage devices. Another embodiment relates to a computer-readable medium that stores (e.g., tangibly embodies) a computer program for carrying out any one of the above-described methods with a computer. In these ways, aspects of the disclosed embodiments enable improved roll control for a device with applications generally to robotic systems and specifically to surgical robotic systems in a computer-assisted medical system.

BRIEF DESCRIPTION OF DRAWINGS

Certain embodiments are illustrated by way of example and not limitation in the figures of the accompanying drawings.

DETAILED DESCRIPTION

Figure 1:
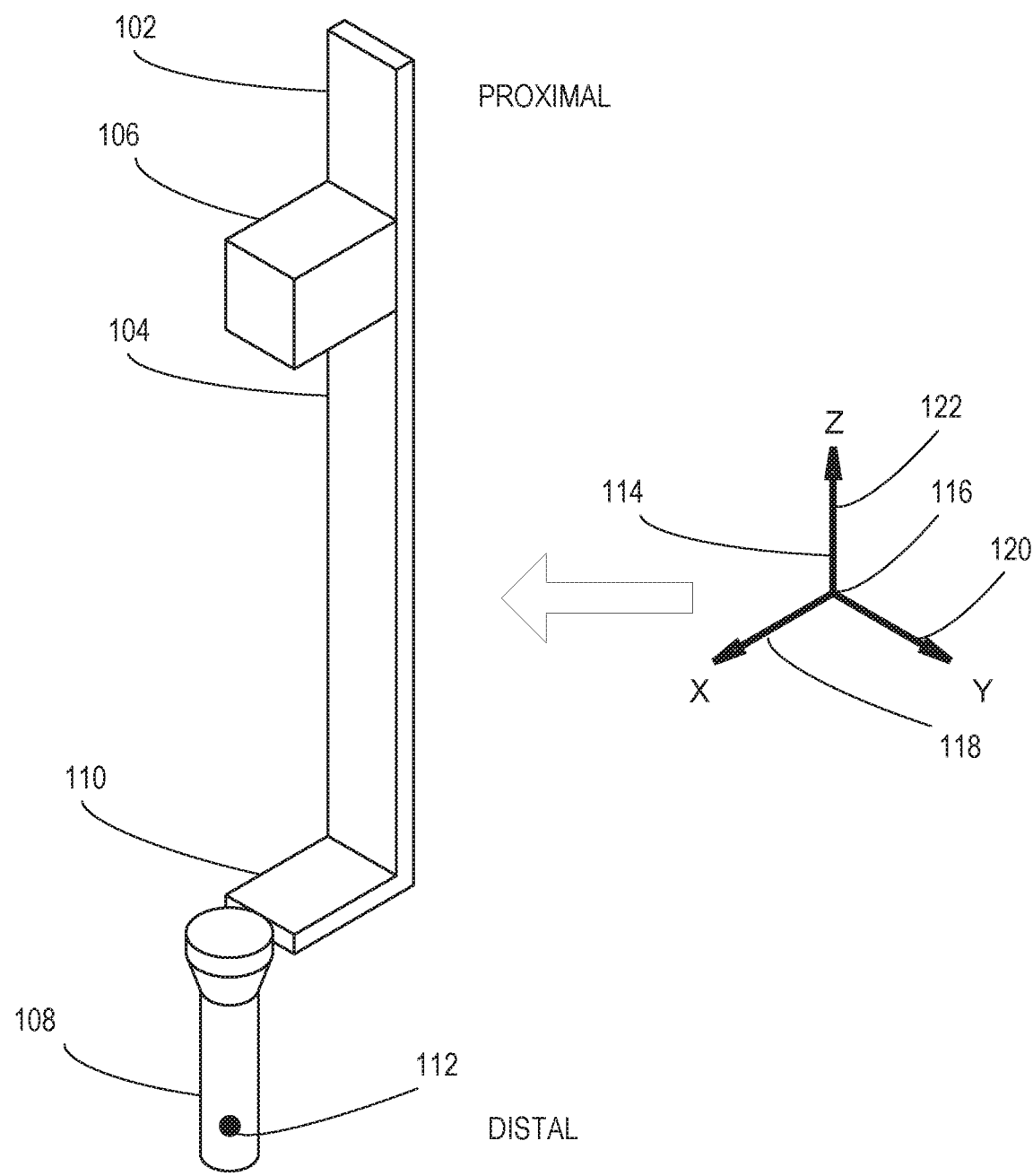
FIG. 1 is a diagram that shows a spar that relates to an example embodiment.

The description that follows includes systems, methods, techniques, instruction sequences, and computer-program products that illustrate embodiments of the present disclosure. In the following description, for purposes of explanation, numerous specific details are set forth in order to provide an understanding of various embodiments of the disclosed subject matter. It will be evident, however, to those skilled in the art that embodiments of the disclosed subject matter may be practiced without these specific details. In general, well-known instruction instances, protocols, structures and techniques have not been shown in detail.

Minimally Invasive Surgery (MIS) can be performed by partially inserting one or more surgical instruments through ports in a patient's body (or body wall). In general, these instruments perform some surgical function and are controlled via an interface on the outside of the body. In some implementations, typically called Robotically Assisted Minimally Invasive Surgery (RAMIS), the surgical instruments can be at least partially teleoperated by surgeons. In a teleoperated surgical system, the surgeon (or surgeons) do not move the instruments by direct physical contact, but instead control instrument motion from some distance away by moving master controllers (or masters). Each surgeon is typically provided with a view of the surgical site via a visual display so that a surgeon may perform some motion on one or more of the masters while viewing the surgical site on the display. Then a related controller of the surgical system causes the surgical instruments to be moved as result of the masters being moved. The instruments and the mechanism that holds them are typically included in a one or more manipulators (e.g., robotic manipulators). A manipulator that may be moved in response to master motion is typically called a slave manipulator (or slave).

In some implementations a personal stereoscopic visual display and one or more masters may comprise a surgeon console. Motions of the masters may be interpreted in the reference frame defined by the visual display and converted to a reference frame defined by an endoscopic camera. As such, motions of the instruments are intuitive to the surgeons controlling them. This mapping, the subsequent control of the manipulators, and any feedback to the master controller, can be facilitated by a computer.

The surgical instruments can then be partially inserted through one or more ports, for example, to treat tissues at surgical sites within the patient. In this context, a port is a general term indicating the position where a surgical instrument enters the patient's body. The port can be artificially created or can be a natural opening. For example, the port can result from an incision or can correspond to a natural body orifice. A multi-port system is one in which there are multiple ports through which one or more respective surgical instruments are inserted into a body of the patient. A single-port system is one in which one or several surgical instruments are inserted through a single port.

In some implementations, a cannula (e.g., a hollow tube) is inserted into a surgical port. The cannula may serve several functions including guiding an instrument through the port, preventing loss of air insufflation from an inflated cavity, allowing fluids and other materials to pass into or out of the body, and reducing trauma to the port site by isolating some motion from the body wall. Since the cannula is tubular, insertion of an instrument and axial rotation of that instrument along its shaft does not induce any motion in the cannula. In non-robotic MIS, translation of a free-floating cannula is typically limited by reaction forces of the body wall pushing on the cannula. In RAMIS, the cannula motion is often further limited by a mechanism holding the cannula, and when this mechanism is on the same manipulator that holds the instrument, it is typically called a spar.

FIG. 1 is a diagram that shows a spar 102 that may be used for certain embodiments that are discussed below. The spar 102 includes a long element 104 that is aligned with a long axis (or spar axis) of the spar 102. At a proximal end of the spar 102 (e.g., towards the robotic attachment), an instrument support element 106 is adapted to support a surgical instrument. At a distal end of the spar 102, a cannula 108 that is also aligned with the long axis of the spar 102 is connected to the long element 104 by a transverse element 110.

Depending on the details of a surgical implementation, a location of the cannula 108 may be designated as a Remote Center of Motion (RCM) 112 so that after the initial insertion of the cannula 108 into a patient's body this location is held spatially fixed at the surgical port with respect to an inertial reference frame. That is, if the patient does not move, fixing the position of the cannula 108 at the port in space is equivalent to fixing the cannula to the patient's body, thereby limiting the forces that the cannula 108 transfers to body wall. However, to complete a surgical operation, some motion of the cannula may be required to place the instrument tip at the proper location inside the body, and as a result the orientation of the cannula 108 at the RCM 112 may change in one or more axial directions (e.g., pitch, roll, yaw). As discussed below in detail, disclosed embodiments enable control about a roll axis aligned with the long axis of the cannula 108 to further minimize motion of the cannula at the RCM 112 in combination with commanded rotations about the pitch and yaw axes.

FIG. 1 also shows a three-dimensional coordinate system 114 that is characterized by an origin 116 and three orthogonal axes including a first axis (or x axis) 118, a second axis (or y axis) 120, and a third axis (or z axis) 122. As is well-known to those skilled in the robotics art, multiple copies of the coordinate system 114 can be attached to various parts of a robotic body. Each body-attached coordinate system 114 for a device can then be used to define a corresponding frame that includes the position of the origin 116 and the orientations of the three axes 118, 120, 122, where these frame values can be characterized with respect to a specified reference frame (e.g., an inertial frame).

Figure 2:
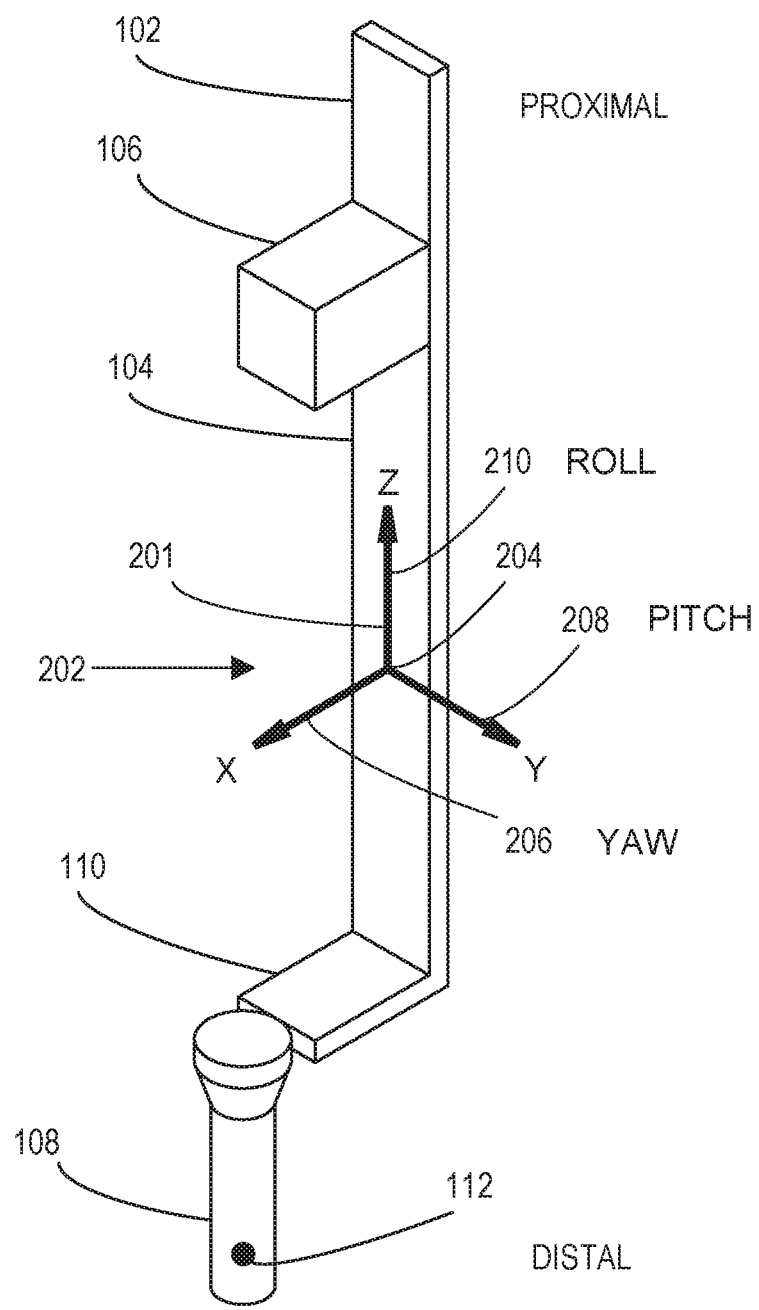
FIG. 2 is a diagram that shows the spar of FIG. 1 with an attached coordinate system.

Typically these frames are defined at connection points (e.g., joints) of a robotic system and with axes aligned with the characteristic geometric features. FIG. 2 is a diagram that shows a body-attached coordinate system 201 that defines a device frame 202 with an origin 204 attached to the spar 102 at a location on the long element 104 (e.g., at the robotic attachment as in FIG. 3). A roll axis 210 (i.e., the z axis 122 in the coordinate system 114 of FIG. 1) is aligned with the long element 104. A yaw axis 206 (i.e., the x axis 118 in the coordinate system 114 of FIG. 1) is aligned with the transverse element 110. A pitch axis 208 (i.e., the y axis 120 in the coordinate system 114 of FIG. 1) is orthogonal to both the long element 104 and the transverse element 110. It should be noted that the roll axis 210 is aligned with a long axis for both the spar 102 and the cannula 108, and these two elements can be understood to have equivalent orientations with corresponding pitch, roll, and yaw axes that are aligned. More generally, a rotational transformation can be used to relate the orthogonal axes for these elements when they are not aligned. In this context, the spar 102 may be considered as an example device whose spatial arrangement is characterized by the device frame 202 including the position of the origin 204 and the orientations of the three axes 206, 208, 210, where the corresponding frame values can be characterized with respect to a specified reference frame (e.g., an inertial frame).

Figure 3:
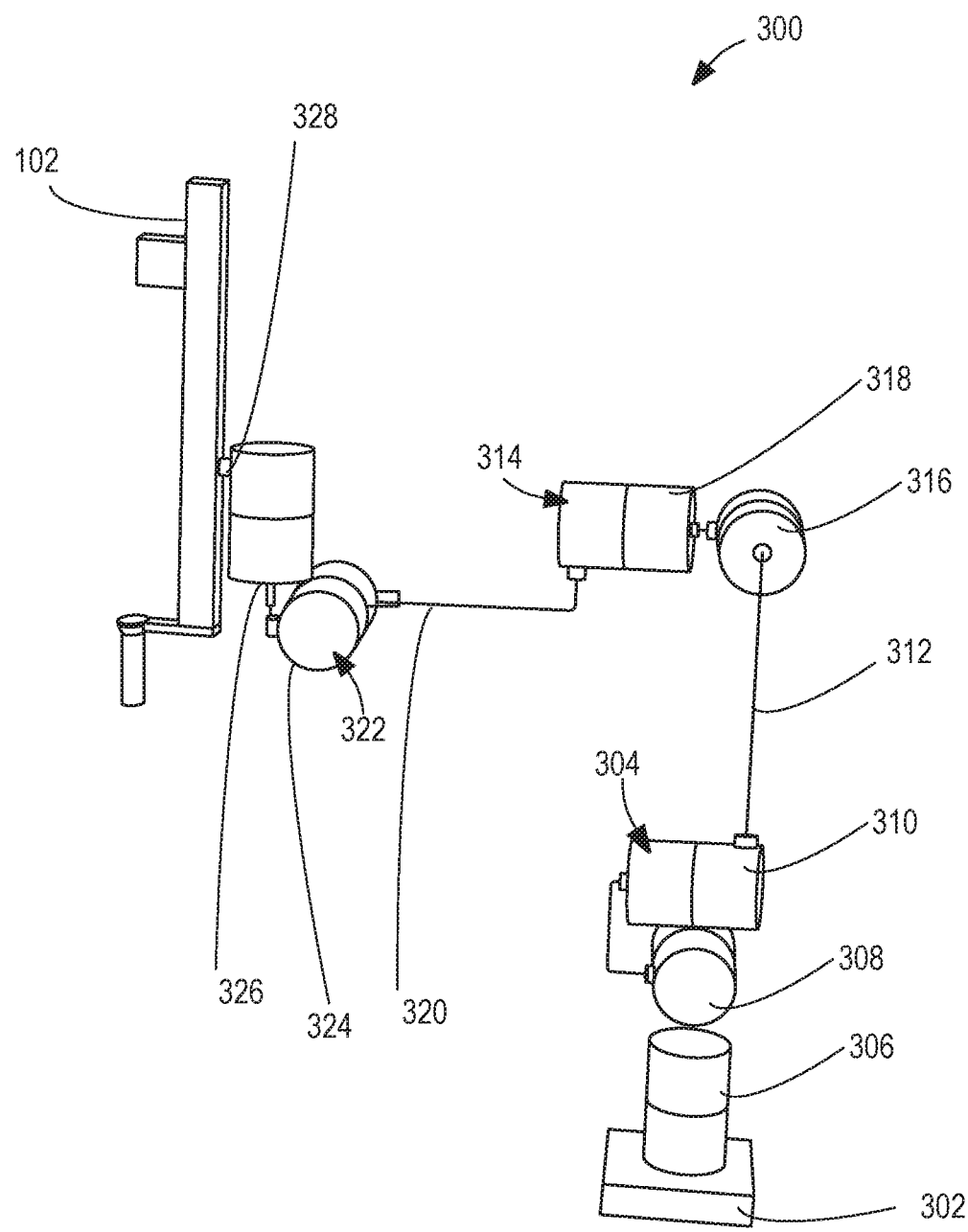
FIG. 3 is a diagram that shows a robotic system that includes the spar of FIG. 1.

FIG. 3 is a diagram that shows a robotic system 300 that includes the spar 102 of FIG. 1. The system includes a base 302 that is typically fixed with respect to an inertial reference frame. A combination shoulder joint 304 includes a shoulder roll joint 306, a shoulder pitch joint 308, and a shoulder yaw joint 310. A first link 312 connects the combination shoulder joint 304 to a combination elbow joint 314 that includes an elbow pitch joint 316 and an elbow roll joint 318. A second link 320 connects the combination elbow joint 314 to a combination wrist joint 224 that includes a wrist pitch joint 324 and a wrist yaw joint 326. The combination wrist joint 224 connects to the spar 102 at a connection point 328 that may correspond to the origin of 204 of the coordinate system 201 of the device frame 202 of FIG. 2.

Figure 4:
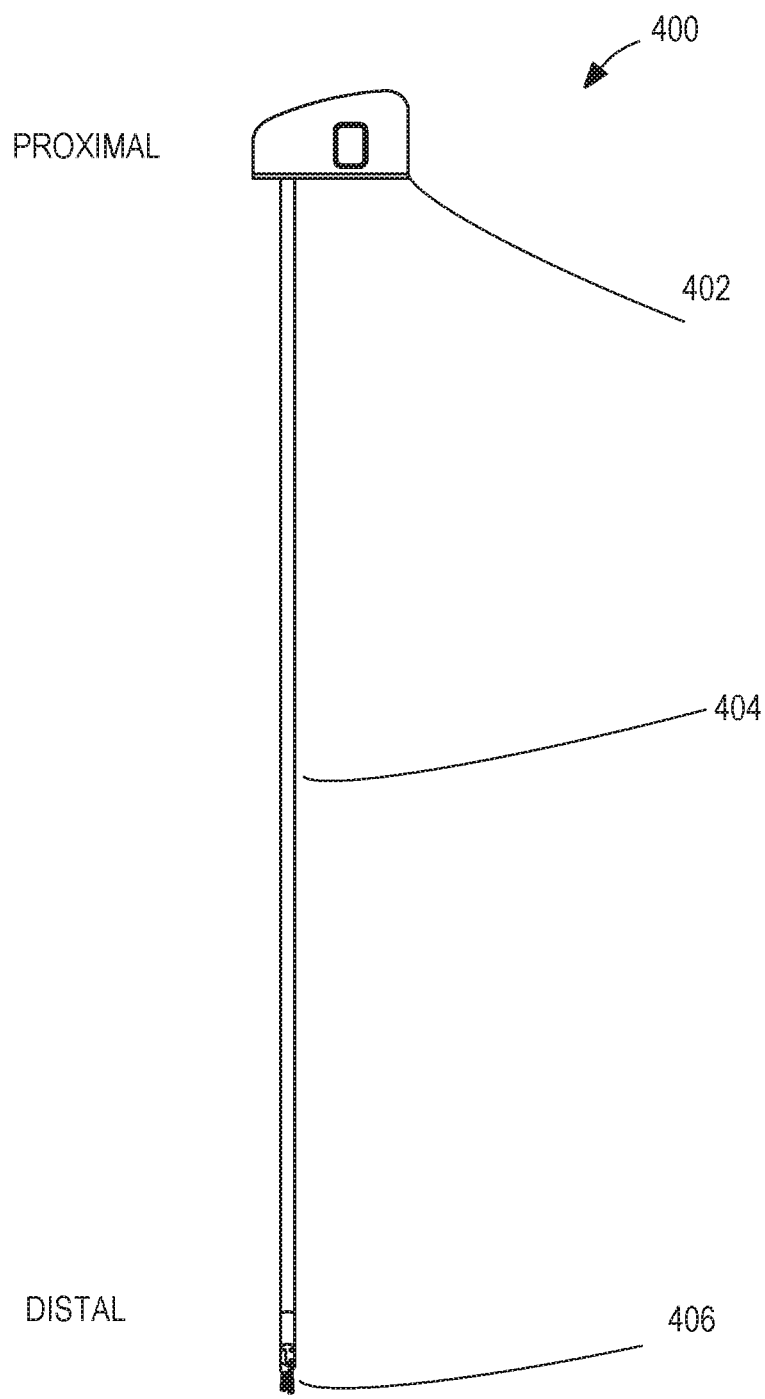
FIG. 4 is a diagram that shows an instrument that may be used in combination with the spar of FIG. 1.
Figure 5:
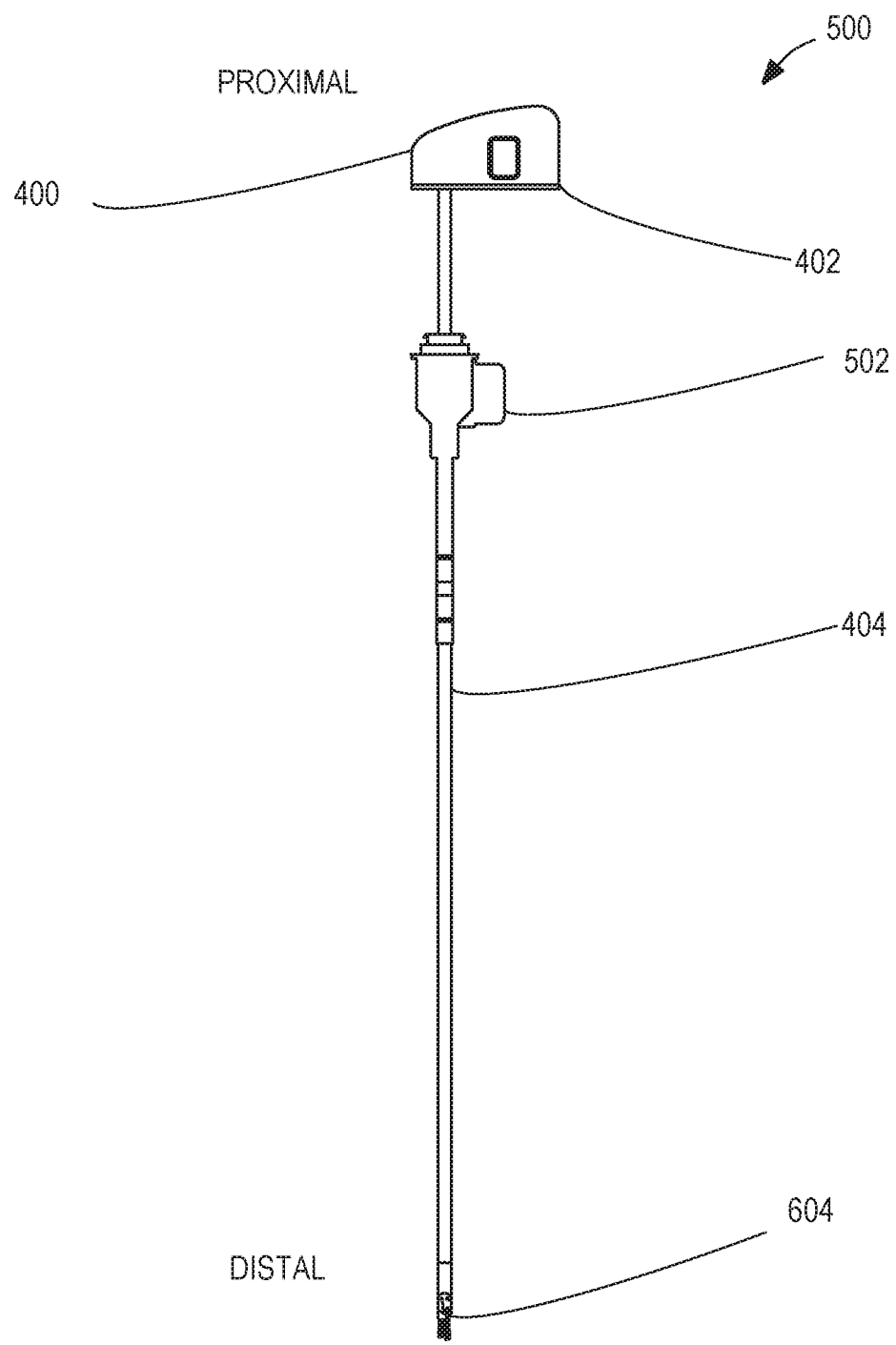
FIG. 5 is a diagram that shows the instrument of FIG. 4 in a configuration that includes a cannula.

FIG. 4 is a diagram that shows an instrument 400 that may be used in combination with the spar 102 of FIGS. 1-3. The instrument 400 includes an instrument backend 402 at a proximal end of the instrument 400 (e.g., towards the robotic attachment) and a shaft 404 that connects the instrument backend 402 to an end effector 406 at a distal end of the instrument 400. FIG. 5 is a diagram that shows the instrument 400 in a configuration 500 that includes a cannula 502 in correspondence to the cannula of 108 of FIGS. 1-3. Although not shown in FIG. 5, the instrument backend 402 may be attached to the spar 102 at the instrument support element 106 of FIGS. 1-3.

Figure 6:
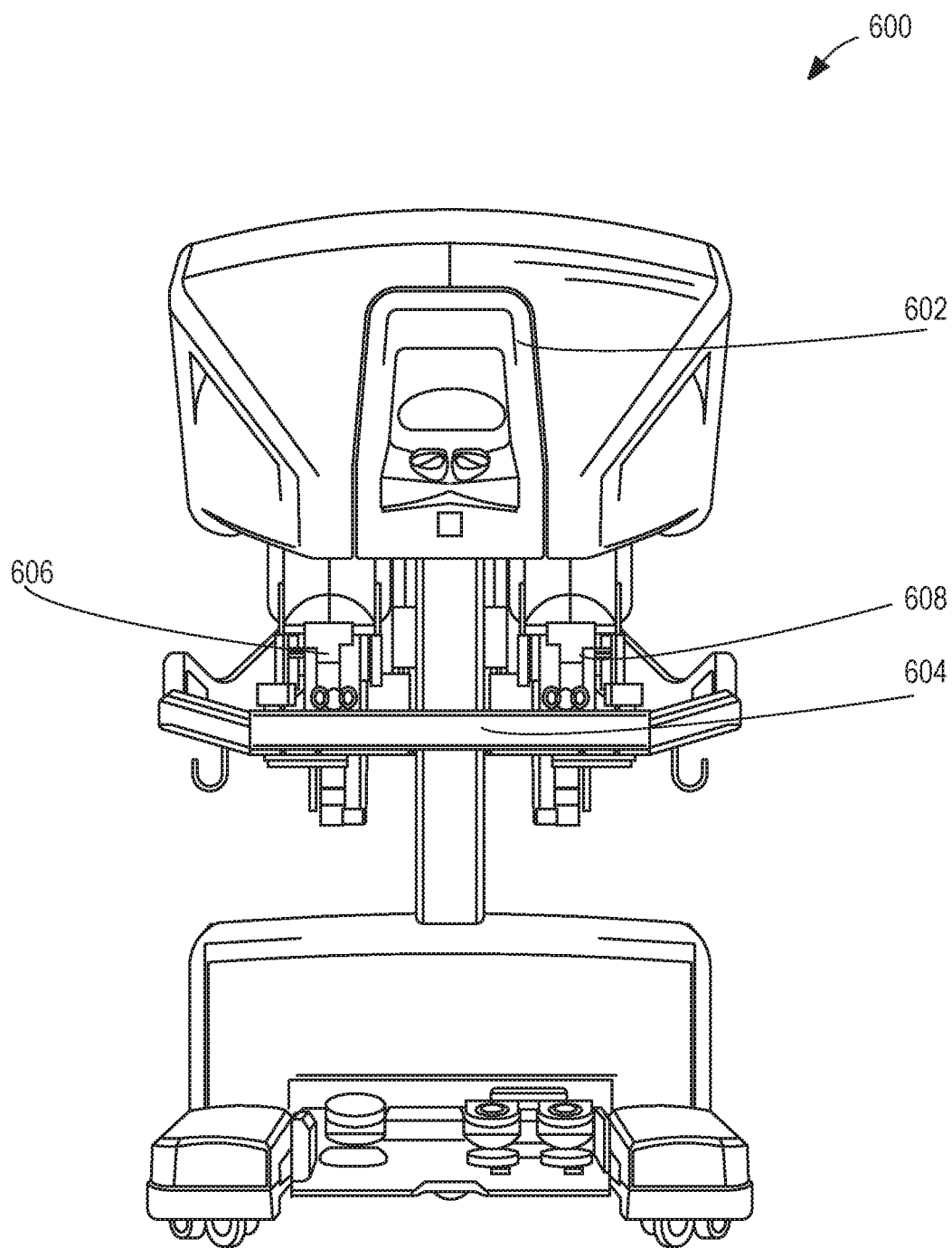
FIG. 6 is a diagram that shows an example surgeon console for an example embodiment.
Figure 7:
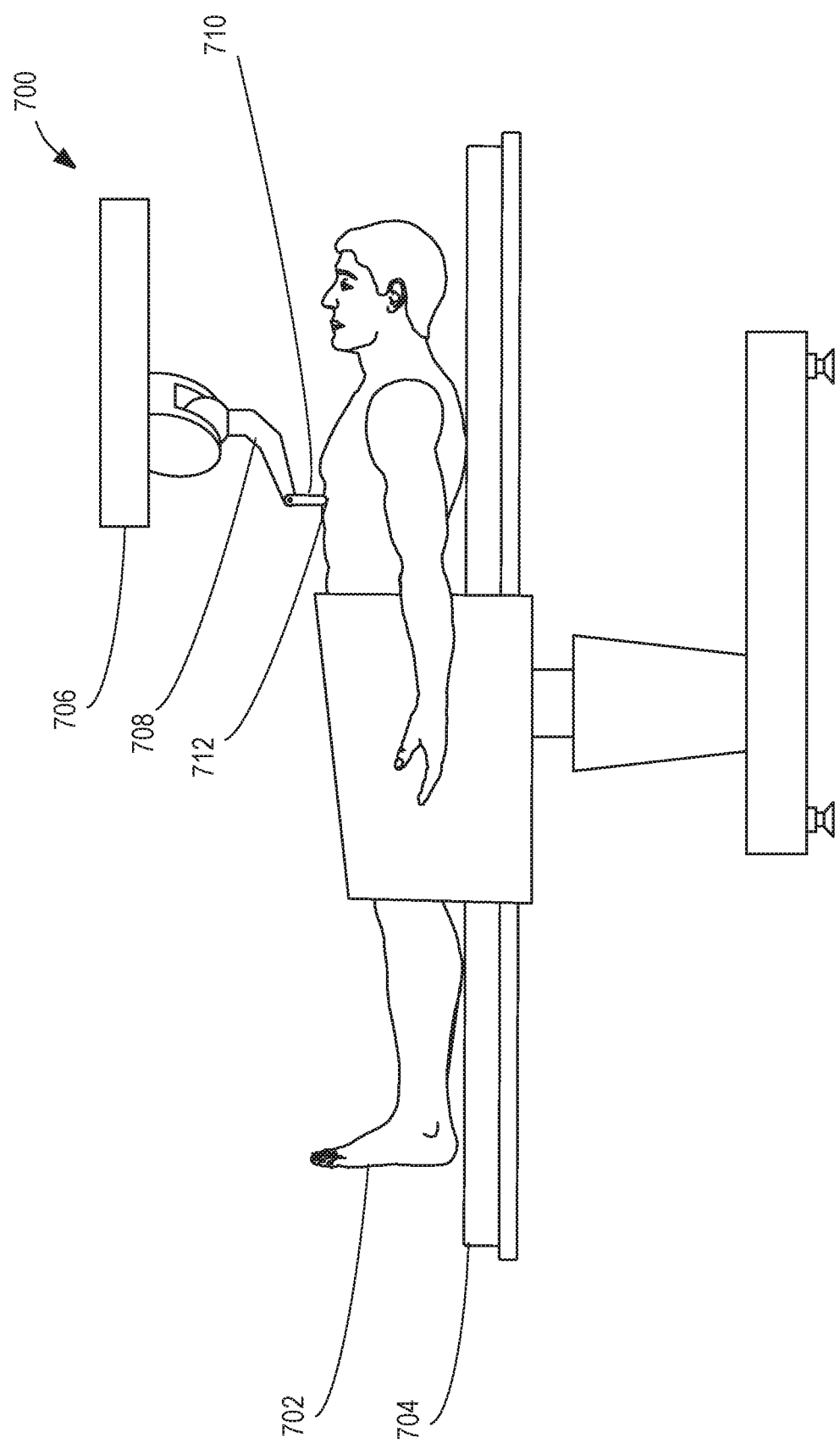
FIG. 7 is a diagram that shows an example surgical station that relates to the surgeon console of FIG. 6.

A broader context for the disclosed embodiments is illustrated in FIGS. 6 and 7. FIG. 6 is a diagram that shows an example surgeon console 600 of a teleoperated surgical system. The surgeon console 600 includes a viewer 602 where an image of a surgical site is displayed to an operator (e.g., the surgeon). A support 604 is provided on which the operator can rest his or her forearms while gripping two master controls 606, one in each hand. The master controls 606 are positioned in a space inwardly beyond the support 604. When using surgeon console 600, the operator typically sits in a chair in front of the console, positions his or her eyes in front of viewer 602 and grips the master controls 606, one in each hand, while resting his or her forearms on support 604. The surgeon console 600 may include a processor that generates signals in response to the motion of the master controls 606.

FIG. 7 is a diagram that shows an example surgical station 700 for the teleoperated surgical system related to FIG. 6. In use, a patient 702 is supported by a surgical table 704 adjacent a manipulator support base 706. The structure supporting the example manipulator support base 706 is not shown in FIG. 7. However, the manipulator support base 706 may be ceiling mounted, supported by a wall of a room in which the surgical station 700 is disposed, mounted to the surgical table 704, or mounted to a cart. In some implementations, the manipulator support base 706 remains in a fixed location over the patient 702 during at least a portion of a surgical procedure. The surgeon console 600 of FIG. 6 is typically positioned at some distance from the surgical station 700, optionally being separated by a few feet within an operating room. In some implementations, surgical station 700 and surgeon console 600 may be separated by a significant distance, optionally being disposed in separate rooms, different buildings, or even greater distances.

The surgical station 700 includes at least one slave manipulator 708 that is supported by the manipulator support base 706. The slave manipulator 708 is configured to support an instrument 710 that enters the patient 702 at a port 712. Although the representation in FIG. 7 is simplified, the slave manipulator 708 may be configured as in the more complex robotic system 300 of FIG. 3, with the base 302 of FIG. 3 corresponding to the manipulator support base 706 of FIG. 7 and the instrument 400 of FIG. 4 corresponding to the instrument 710 of FIG. 7. As discussed above, after an initial placement of the cannula 108 of FIG. 1, the spatial location of the portion of the cannula 108 at the port 712 is typically held fixed as an RCM 112 in order to avoid unnecessary stress on the patient 702. Then, in order to orient the cannula 108 (and the related instrument 400 of FIG. 4) within the patient's body, addition pitch and yaw rotations are typically required as measured by the body-attached yaw axis 206 and pitch axis 208. However, as discussed below, these pitch and yaw motions can induce rotations about the roll axis 206 where these roll-axis rotations may cause additional stress at the RCM 112.

Figure 8:
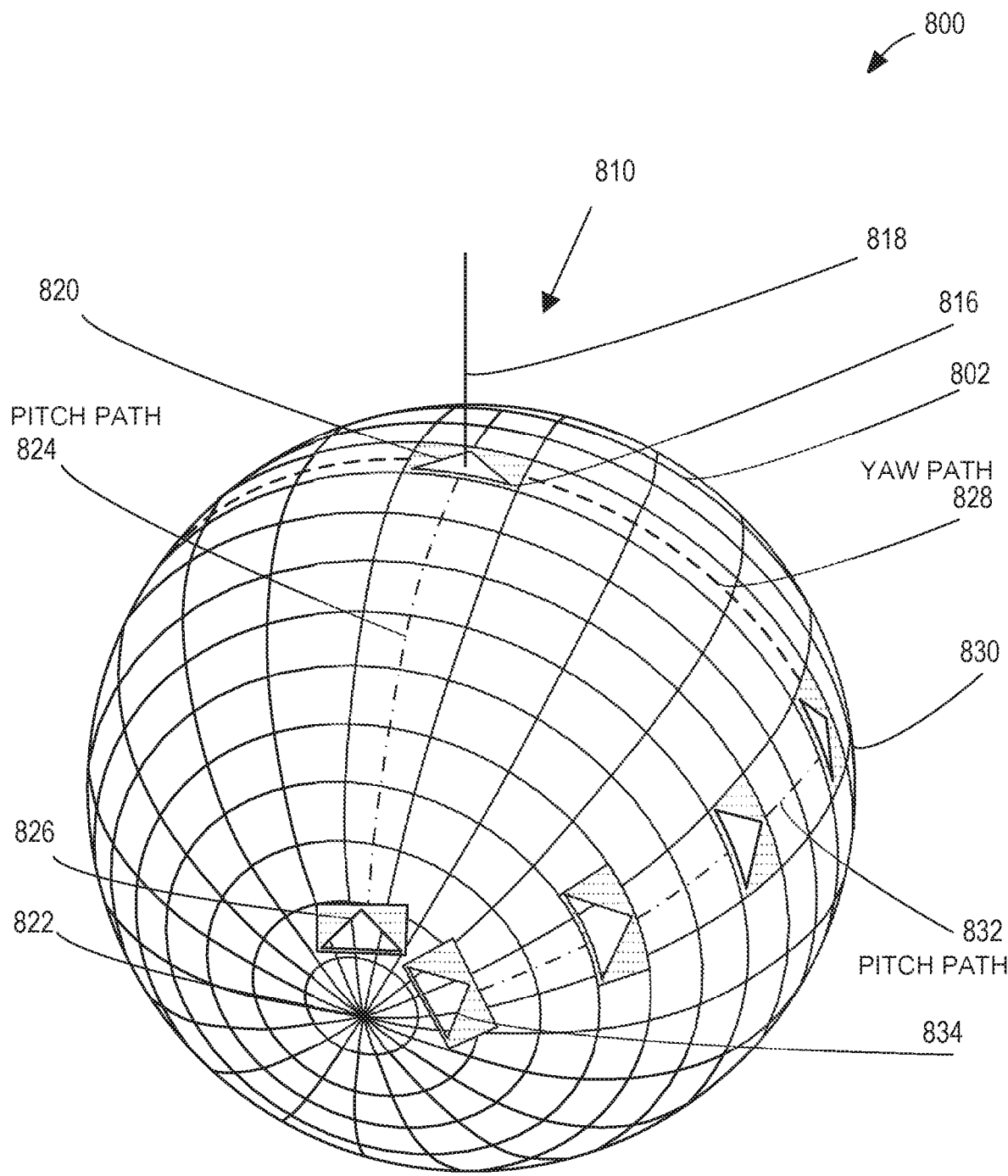
FIG. 8 is a diagram that shows a spherical map of spar roll that relates to the spar of FIG. 1.
Figure 9:
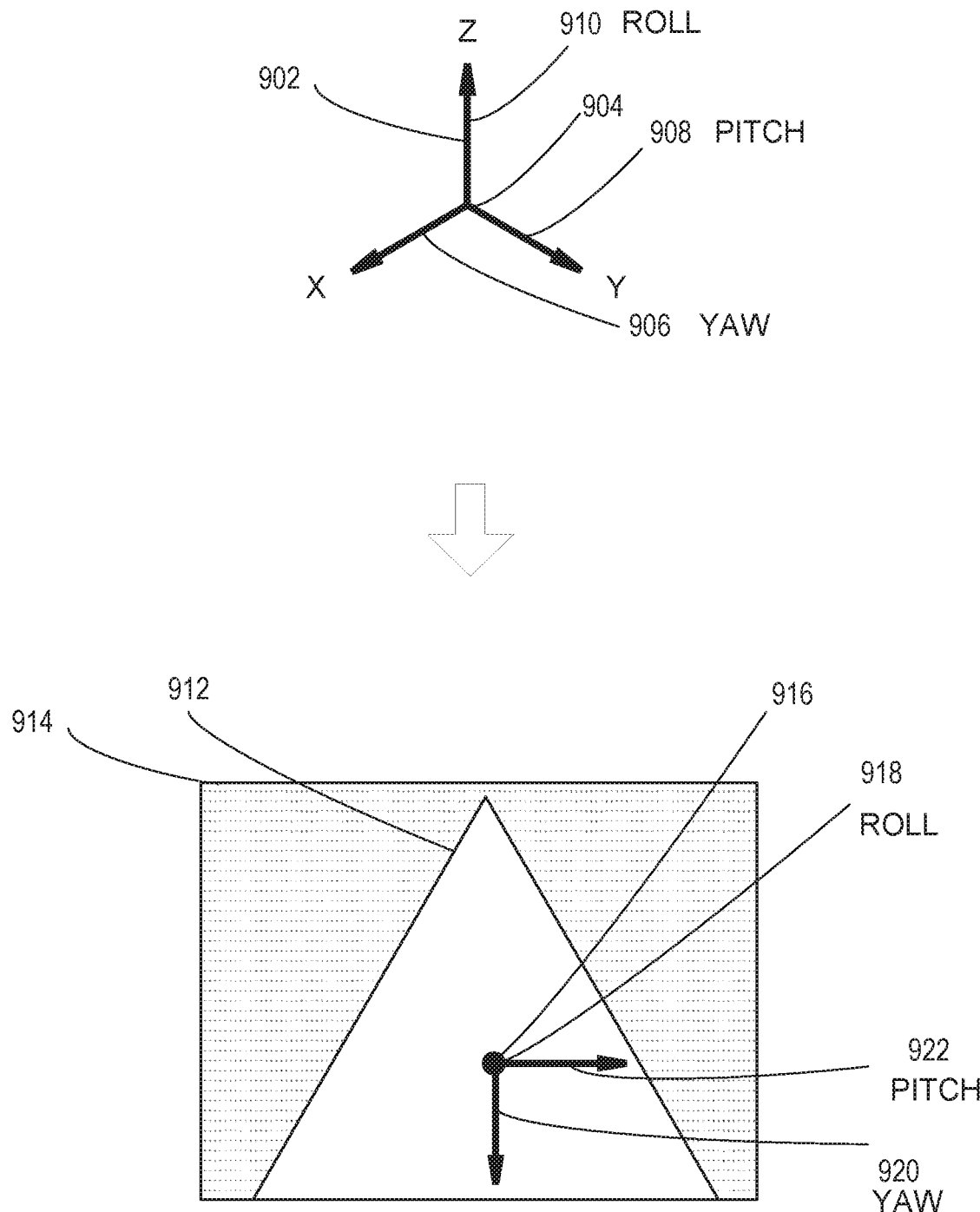
FIG. 9 is a diagram that shows details related to the spherical maps of FIGS. 8, 10, and 11.

FIG. 8 is a diagram that shows spherical map 800 of spar roll for a given pitch and yaw, which are measured angularly on the surface of a sphere 802, in accordance with the graphical representation in FIG. 9. FIG. 9 shows an orthogonal coordinate system 902 including an origin 904, a yaw axis 906, a pitch axis 908, and a roll axis 910. The orientation of this coordinate system 901 can be represented by the arrangement of a triangular element 912 in a surface element 914, where a central location 916 of the surface element 914 corresponds to the origin 904 of the coordinate system 902, the roll axis 918 is an outward normal from the surface element 914, the yaw axis 920 is directed towards the triangular-element side aligned with an edge of the surface element 914, and the pitch axis 922 is orthogonal to the yaw axis 920 and the roll axis 918 with the direction shown in FIG. 9. A given assignment of surface elements 914 on a surface such as the sphere 802 then defines a map that specifies roll at each point of the surface.

In FIG. 8 this representation is used to show the orientation of the spar 102 of FIG. 1 (or a rigid body generally) with the origin 904 of a body-attached coordinate system 902 at the center of the sphere 802. A reference orientation 810, which is typically defined as the orientation of the spar 102 at zero pitch and yaw (e.g., close to the center of the manipulator's range), is represented by a surface element 816 including a triangular element 820 in accordance the representation of FIG. 9. Additionally the outward normal corresponding to the roll axis 818 for the reference orientation 810 is also shown.

This reference orientation 810 can be used as a nominal value for characterizing subsequent changes in the orientation of the spar 102. For example, a roll-angle offset can be defined as an angular deviation about the roll axis 818 of the reference orientation 810. As discussed below, variations in pitch and yaw will induce roll-angle offsets that may be discontinuous or multi-valued at various points in the angular command space for pitch and yaw. More generally, a corresponding reference frame defined by a body-attached coordinate system 902 for the reference orientation 810 can be used to characterize the spatial arrangement of the spar 102 as it moves (e.g., via the device frame 202 of FIG. 2). Typically the reference frame is assumed to be an inertial frame or at least referenced to an inertial frame.

As the orientation of the spar 102 is changed by variations in pitch and yaw from the reference orientation 810, the current roll axis 918 is represented by the normal to a corresponding surface element 914 and the relative position of the triangular element 912 within the surface element 914 represents the current amount of roll-angle offset relative to the reference orientation 810 (e.g., rotation about the reference roll axis 818).

In general, the parallel lines of latitude on this spherical map 800 represent variations in yaw at constant pitch while the converging lines of longitude represent variations in pitch at constant yaw with the reference orientation 810 (i.e., at surface element 816) being identified as $\theta_{pitch}=90°$ and $\theta_{yaw}=0°$. Small deviations in pitch and yaw from reference orientation 810 result in small deviations in roll. However, the kinematic parameterization becomes singular (e.g., multivalued) at exactly $\theta_{pitch}=0°$ and $\theta_{pitch}=180°$, the poles of the sphere 802, as indicated by the singularity 822 at $\theta_{pitch}=0°$. A first path 824 ("Pitch Path") represents a pure pitch movement from the reference orientation 810 to a first orientation 826 near the singularity 822. A second path 828 ("Yaw Path") represents a pure yaw movement from the reference orientation 810 to a second orientation 830 at $\theta_{yaw}\sim72°$. A third path 832 ("Pitch Path") represents a pure pitch movement from the second orientation 830 to a third orientation 834 near the singularity 822. Although the roll-angle offset is single-valued away from the singularity 822, a comparison between the first orientation 826 and the third orientation 834 shows that small deviations in pitch and yaw near the singularity 822 can result in large roll motions of the spar 102 and likewise the cannula 108 of FIG. 1. That is, near the singularity 822, the roll-angle offset that determines the relative orientations of the yaw axis 206 and the pitch axis 208 relative to the roll axis 210 of the spar 102 (as shown in FIG. 2) may be path dependent.

Figure 10:
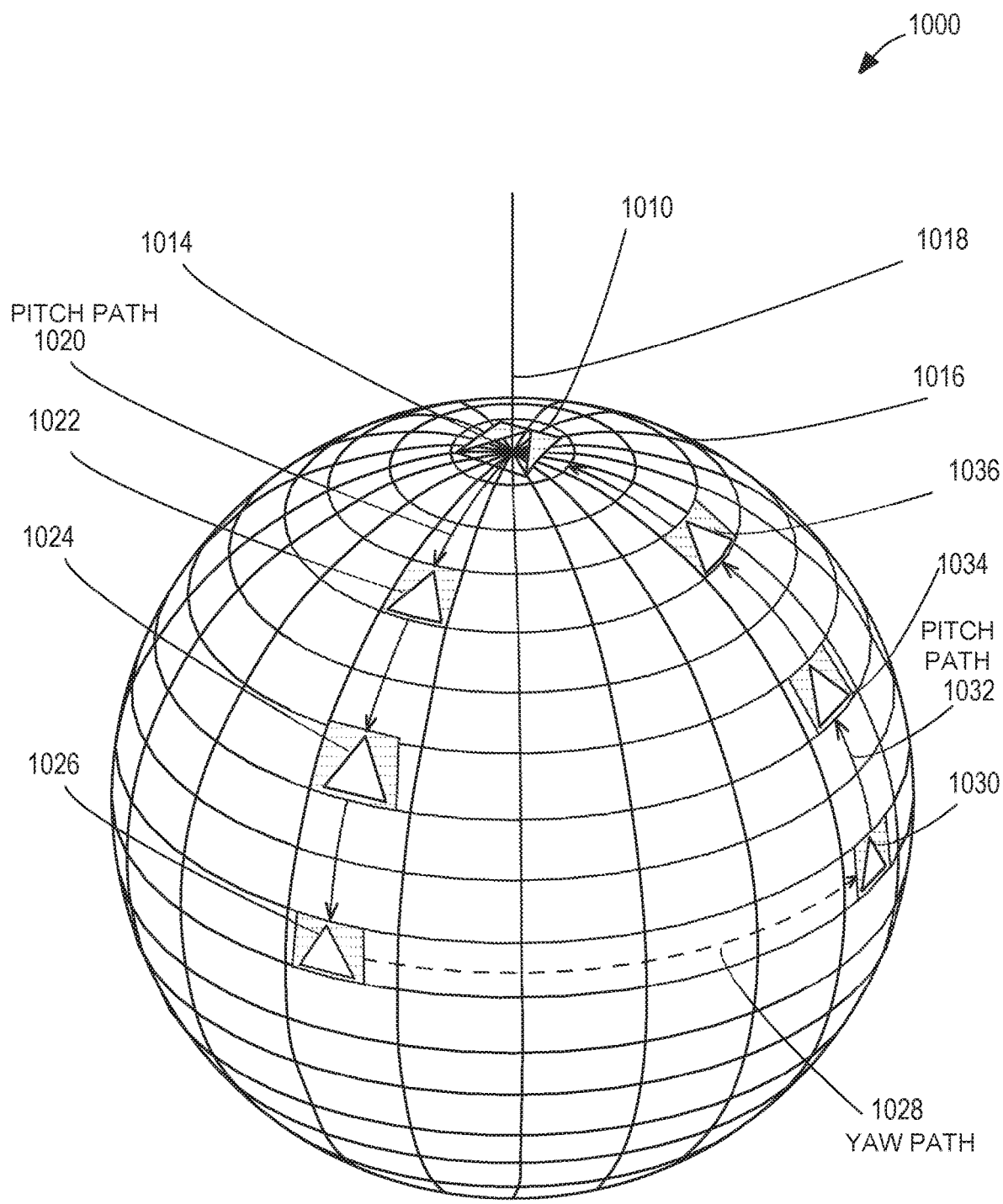
FIG. 10 is a diagram that shows another spherical map of spar roll that relates to the spar of FIG. 1.

FIG. 10 is a diagram that shows another spherical map 1000 of spar roll for a given pitch and yaw in accordance with the graphical representation in FIG. 9. In this case a roll axis 1018 corresponding to the reference orientation 1010 is shown at a reference node 1014 that corresponds to a singularity of the spherical map 1000 at the north pole of the sphere 1016. Because of the singularity at the reference node 1014, the roll-angle offset that determines the relative orientations of the yaw axis 206 and the pitch axis 208 relative to the roll axis 210 of the spar 102 (as shown in FIG. 2) may be path dependent (e.g., multivalued).

A reference orientation 1010 can be defined to be consistent with the orientations along a first path 1020 in FIG. 10. The first path 1020 ("Pitch Path") represents a pure pitch movement from the reference orientation 1002 to a first orientation 1022, then to a second orientation 1024, and then to a third orientation 1026 near the lower portion of the upper hemisphere, where these orientations 1022, 1024, 1026 have zero roll-angle offset relative to the reference orientation 1010. A second path 1028 ("Yaw Path") represents a pure yaw movement from the third orientation 1026 to a fourth orientation 1030. A third path 1032 ("Pitch Path") represents a pure pitch movement from the fourth orientation 1030 to a fifth orientation 1034, then to a sixth orientation 1036 near the singularity at reference node 1014. Although the roll-angle offset is single-valued along these paths 1020, 1028, 1032, a comparison between the first orientation 1022 and the sixth orientation 1036 shows that the roll-angle offset is discontinuous (or multi-valued) at the reference node 1014.

Figure 11:
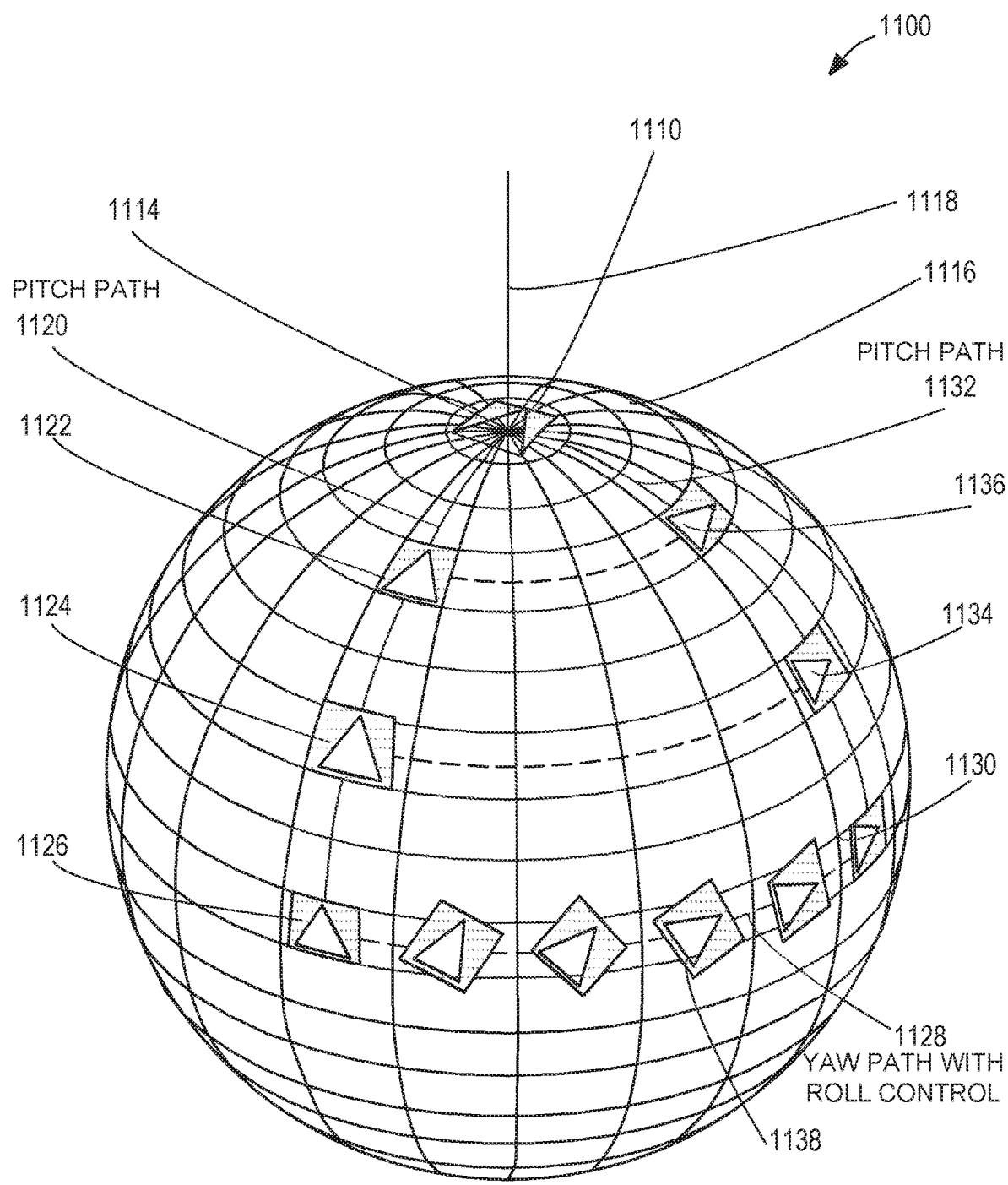
FIG. 11 is a diagram that shows another spherical map of spar roll that relates to an embodiment for controlling roll for a device that includes the spar of FIG. 1.

FIG. 11 illustrates an example embodiment for controlling the roll-angle offset to maintain continuity everywhere in the pitch-yaw space. FIG. 11 is a diagram that shows another spherical map 1100 of spar roll for a given pitch and yaw in accordance with the graphical representation in FIG. 9. Similarly as in FIG. 10, a roll axis 1118 corresponding to the reference orientation 1110 is shown at a reference node 1114 that corresponds to a singularity of the spherical map 1100 at the north pole of the sphere 1116. Because of the mathematical singularity at the reference node 1114, the roll-angle offset that determines the relative orientations of the yaw axis 206 and the pitch axis 208 relative to the roll axis 210 of the spar 102 (as shown in FIG. 2) may be path dependent. As discussed below, this indeterminacy can be corrected by roll control about the roll axis 210 in accordance with example embodiments.

Similarly as in FIG. 10, a reference orientation 1110 can be defined to be consistent with the orientations along a first path 1120 in FIG. 11. The first path 1120 ("Pitch Path") represents a pure pitch movement from the reference orientation 1110 to a first orientation 1122, then to a second orientation 1124, and then to a third orientation 1126 near the lower portion of the upper hemisphere, where these orientations 1122, 1124, 1126 have zero roll-angle offset relative to the reference orientation 1110. A second path 1128 ("Yaw Path with Roll Control") represents a roll-controlled yaw movement from the third orientation 1126 to a fourth orientation 1130. A third path 1132 ("Pitch Path") represents a pure pitch movement from the fourth orientation 1130 to a fifth orientation 1134, then to a sixth orientation 1136 near the reference node 1114. In this case (unlike the example of FIG. 10), a comparison between the first orientation 1022 and the sixth orientation 1136 shows that the roll-angle offset is continuous at the reference node 1114.

Along the second path 1128 the roll-angle offset is controlled to an orientation 1138 that corresponds to a roll-free rotation from the reference orientation 1110 at the reference node 1114 to the yaw-pitch combination indicated by a point on the second path 1128. For example, let $_{device}^{reference}R$ be a 3×3 rotation matrix whose columns are the unit vectors for the coordinate system 201 of the body-attached device frame 202, where these unit vectors are expressed in the coordinates of the reference orientation 1110. As in FIG. 2, the x, y and z axes are respectively identified with yaw 206, pitch 208, and roll 210. That is, the unit vectors for yaw, pitch, and roll in the device frame 202 are each expressed as a combination of the unit vectors for yaw, pitch and roll in the reference frame. Then $^{device}P$ (a position vector in the device frame 202) can be expressed in the reference frame corresponding to the reference orientation 1110 as $$^{reference}P = {}_{device}^{reference}R \cdot {}^{device}P. \quad (1)$$

Next, the rotation matrix $_{device}^{reference}R$ is expressed as a combination of a roll-axis-alignment rotation from the reference frame and a rotation about the roll axis:

$$_{device}^{reference}R = {}_{alignment}^{reference}R(\hat{k},\theta) \cdot {}_{device}^{alignment}R(\hat{e}_z,\alpha). \quad (2)$$

The roll-axis-alignment rotation matrix $_{ralignment}^{reference}R(\hat{k},\theta)$ rotates from the reference coordinates to an alignment frame by a single axis rotation about some combination of pitch and yaw in the reference frame, where the rotation axis $\hat{k}=(k_x, k_y, 0)^T$ and the rotation angle θ are determined to align the z-axis of the of the alignment frame with the z-axis of the desired or measured device frame. For example, let $_{device}^{reference}M$ be a measured value of the device frame from the reference frame. Then $\hat{k}$ and θ can be determined from the single-axis rotation (or quaternion) that aligns the z-axes of the two matrices:

$$\left[ {}_{alignment}^{reference}R(\hat{k}, \theta) \right]_z = \left[ {}_{device}^{reference}M \right]_z. \quad (3)$$

The roll rotation matrix $_{device}^{alignment}R(\hat{e}_z,\alpha)$ rotates from the alignment frame about the roll axis $\hat{e}_z=(0, 0, 1)^T$ by an roll-angle offset α that can be specified according to the details of the implementation. In the embodiment of FIG. 11, for example, the roll-angle offset α is zero so that $_{device}^{alignment}R$ the identity matrix. Alternatively, more complex adjustments in the roll-angle offset can be made dynamically including smooth transitions from one set point to another.

Figure 12:
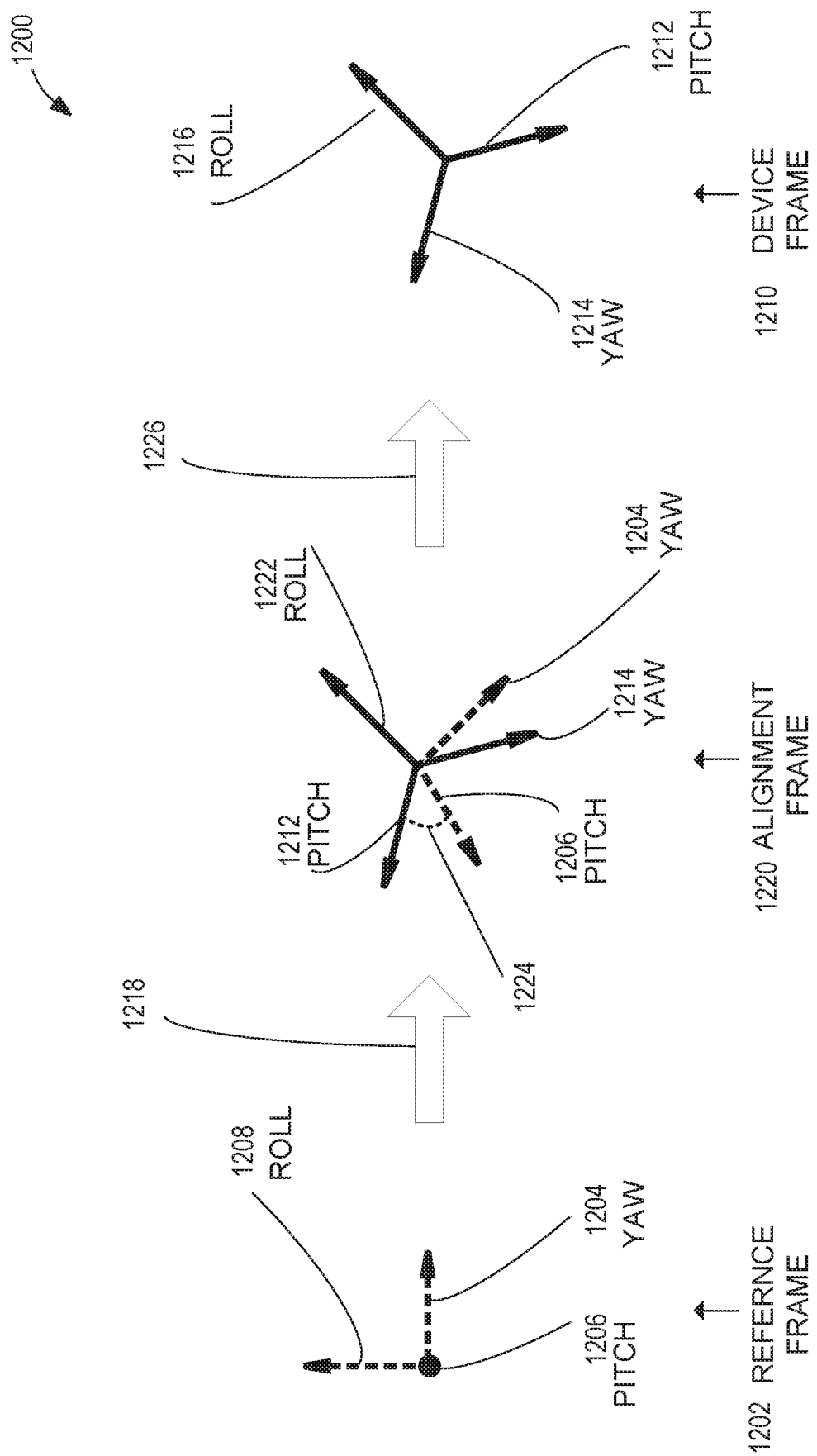
FIG. 12 is a diagram that shows a sequence of operations for controlling roll according to the embodiment of FIG. 11 and related embodiments.

FIG. 12 shows an example mapping 1200 from reference-frame coordinates 1202 including yaw axis 1204, pitch axis 1206 (out of the page), and roll axis 1208 to device-frame coordinates 1210 including yaw axis 1214, pitch axis 1212, and roll axis 1216. A roll-axis-alignment rotation 1218 (e.g., based on Eq. 3) from the reference-frame coordinates 1202 to alignment-frame coordinates 1220 aligns the roll axes 1208, 1216 to a common roll axis 1222, so that the respective pitch axes 1206, 1212 and yaw axes 1204, 1214 are separated by a roll-angle offset 1224 about the common roll axis 1222. A roll rotation 1226 from the alignment-frame coordinates 1220 to the device-frame coordinates 1210 compensates for the given roll-angle offset 1224 to align the alignment-frame coordinates 1220 with then device-frame coordinates 1210. As noted above, the roll rotation 1226 can be specified independently of the measured device coordinates depending on the details of the implementation (e.g., with magnitude as in Eq. 2).

As demonstrated by the paths shown in FIGS. 8 and 10, an uncontrolled roll-angle offset 1224 can lead to discontinuous or multivalued parameterizations of the spar orientation. By controlling for the roll-angle offset 1224 in combination with pitch and yaw displacements along the second path 1128 in FIG. 11, the rotation about the roll axis 1222 is controlled so that the orientation 1138 corresponds to the roll-free rotation in Eq. 3 from the reference orientation 1110. In this way the roll-axis component of the orientation 1138 for each yaw-pitch value along the second path 1128 is normalized with respect to the reference orientation 1110. As illustrated in FIG. 11, this normalization works similarly for other paths such at the path from the second orientation 1124 to the fifth orientation 1134 and the path from the first orientation 1111 to the sixth orientation 1136.

Figure 13:
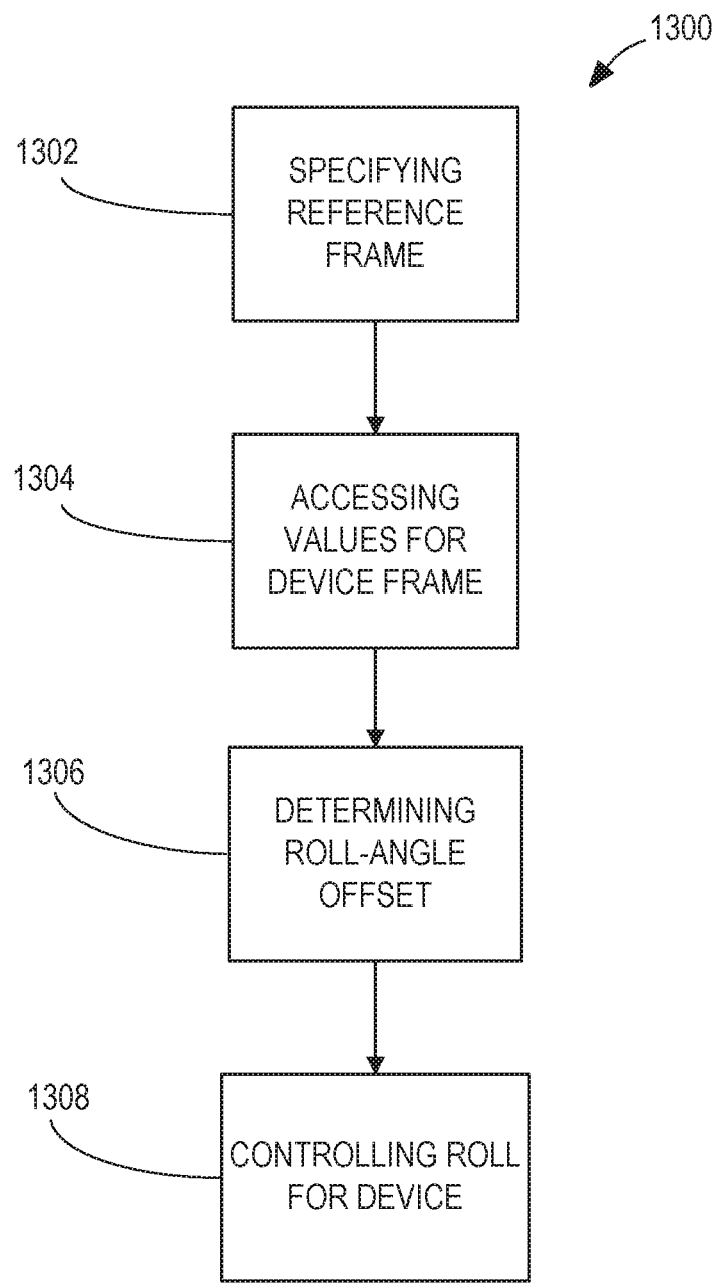
FIG. 13 is a flowchart that shows a method of controlling roll for a device such as the spar of FIG. 1 in accordance with an example embodiment.

FIG. 13 is a flowchart that shows a method 1300 of controlling roll for a device (e.g., spar 102 in FIGS. 1-2) in accordance with the embodiments of FIGS. 11 and 12. A first operation 1302 includes specifying a reference frame 1202 that corresponds to a reference orientation for the device, where the reference frame 1202 includes a reference yaw axis 1204, a reference pitch axis 1206, and a reference roll axis 1208.

A second operation 1304 includes accessing values for a device frame 1210 that corresponds to an orientation of the device, where the device frame 1210 includes a device yaw axis 1214, a device pitch axis 1212, and a device roll axis 1216. For the embodiment of FIG. 2, the device may be identified with the spar 102. In applications to robotics generally, the device may be characterized as a robotic element or a robotically-supported instrument.

A third operation 1306 includes determining a roll-angle offset 1224 that characterizes an angular difference about the device roll axis 1222 between the device frame 1210 and a roll-axis-alignment rotation 1218 of the reference frame 1202, where the roll-axis-alignment rotation 1218 corresponds to a rotation about a combination of the reference yaw axis 1204 and the reference pitch axis 1206 to align the reference roll axis 1208 with the device roll axis 1216 (e.g., as a common roll axis 1222). Depending on the operational setting, the roll-angle offset 1224 may be determined as a pre-defined specified value (e.g., zero or below a threshold value). Alternatively the roll-angle offset may be based on a measured value for the device at a given time.

A fourth operation 1308 includes controlling roll for the device by rotating the device by an amount corresponding to the roll-angle offset 1224 about the device roll axis 2116 (e.g., identified as the common roll axis 1222 in FIG. 12). As illustrated by FIG. 11, the roll-axis component of the orientation 1138 is thereby normalized for a given yaw-pitch value with respect to the reference orientation 1114. In a robotics embodiment, for example, controlling the roll for the device may include transmitting at least one command to at least one actuator for rotating the device about the device roll axis 210. For example, the device may be rotated to maintain a specified roll-angle offset. Alternatively, the device may be rotated by an amount corresponding to a difference between a value determined at a given time (e.g., by measurement) and a specified roll-angle offset. More generally, the control operations may be based on a comparison between the determined roll-angle offset at a given time and a specified roll-angle offset. As described above, roll control may be carried out independently of control for pitch and yaw in some operational settings.

In this context, the difference between the device frame 1210 and the reference frame 1202 includes a yaw-angle offset $\beta_{yaw}$ relative to the reference yaw axis 1204, a pitch-angle offset $\beta_{pitch}$ relative to the reference pitch axis 1206, and possibly a non-zero a roll-angle offset $\beta_{roll}$ relative to the reference roll axis 1208. In the roll-axis-alignment rotation 1218, the roll-angle offset $\beta_{roll}$ is ignored to avoid inducing roll through displacements in pitch and yaw. That is, the roll-axis-alignment rotation corresponds to a rotation for the yaw-angle offset $\beta_{yaw}$ about the reference yaw axis 1204, a rotation for the pitch-angle offset $\beta_{pitch}$ about the reference pitch axis 1206, and no rotation about the reference roll axis 1208 in correspondence to the rotation axis $\hat{k}=(k_x, k_y, 0)^T$ and the rotation angle $\theta$ as discussed above with respect to Eq. 3.

Figure 14:
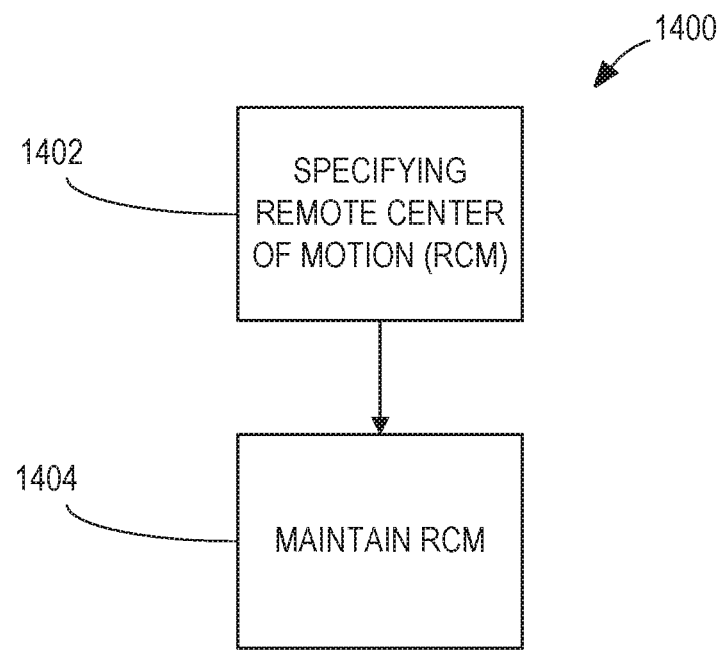
FIG. 14 is a flowchart that shows a method of maintaining a position of a Remote Center of Motion (RCM) in accordance with an example embodiment that is related to the embodiment of FIG. 13.

Optionally an RCM 112 (e.g., as at the cannula 108 of FIGS. 1-2) may be specified so that motions are also constrained to keep the RCM 112 fixed relative to the reference frame 1013. As previously noted, the spar 102 and the cannula 108 in FIGS. 1-2 typically have equivalent orientations with corresponding yaw, pitch, and roll axes 206, 208, 210 that are aligned. FIG. 14 is a flowchart that shows a related method 1400 for maintaining a position of the RCM 112. A first operation 1402 includes specifying an RCM 112 at a given location of the device, the RCM corresponding to an origin of the device frame. A second operation 1404 includes maintaining the RCM 112 at a given location in the reference frame while controlling roll for the device by controlling the roll-angle offset about the device roll axis.

In some operational settings, roll control may be performed after first detecting the device orientation without roll control and then controlling roll for the device at some response rate. In one related embodiment, for example, the accessed values for the device frame 1210 determine a first orientation of the device at a first time, and a rotation of the device from the first orientation by the amount corresponding to the roll-angle offset about the device roll axis 1216 determines a second orientation of the device, where the second orientation corresponds to values for the device frame 1210 at a second time. Similarly, the device may start from a prior orientation (not necessarily the reference orientation) and then be commanded by a combination of yaw-pitch rotations with the roll being controlled by the roll-angle offset control at some response rate.

Figure 15:
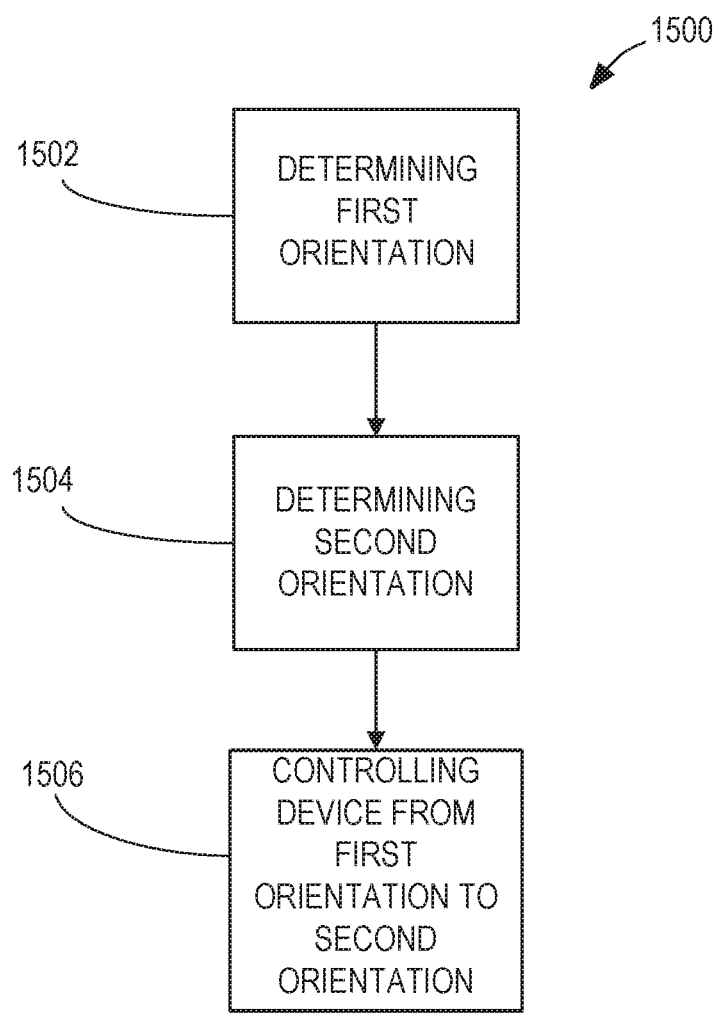
FIG. 15 is a flowchart that shows a method of controlling a device from controlling the device from a first orientation to a second orientation in accordance with an example embodiment that is related to the embodiment of FIG. 13.

FIG. 15 is a flowchart that shows a related method 1500 that includes operations between two orientations for the device for an example embodiment. A first operation 1502 includes determining a first orientation of the device from the accessed values for the device frame at a first time, the first orientation corresponding to a first roll-angle offset about the device roll axis. A second operation 1504 includes specifying a second orientation corresponding to a second roll-angle offset about the device roll axis. A third operation 1506 includes controlling the device from the first orientation to the second orientation by controlling the roll-angle offset about the device roll axis from the first roll-angle offset to the second roll-angle offset in combination with operations for controlling the device about the device pitch axis and device roll axis from the first orientation to the second orientation.

As discussed above, the reference frame 1202 and the roll-angle offset 1224 can be set arbitrarily and repeatedly depending on the details of the operational setting. For example, the specification of a reference frame 1202 may be based on a manually moving a robotic element (e.g., the spar 102 of FIGS. 1-2) to a new position and orientation in a clutch mode where the robotic element can be freely moved. In addition, these values may be specified at set points of a surgical procedure including the initial insertion of a surgical instrument into a patient (e.g., as in FIG. 7) as well as subsequent initialization stages in of the procedure. For example, after the specification of a first reference frame based on a first position and orientation of the device, the roll-angle offset may be controlled with respect to that first reference frame until disengagement at a later time. The device may then be manually moved to second position and orientation that define a define a second reference frame, so that the roll-angle offset may be controlled with respect to the second reference frame for a period of time, and so on.

Figure 16:
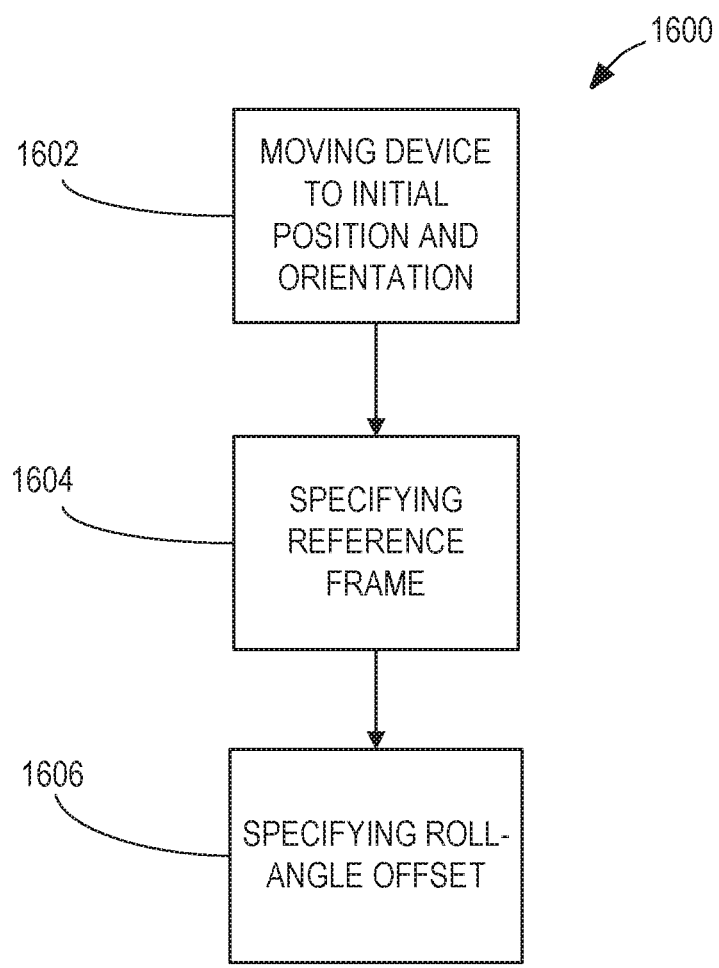
FIG. 16 is a flowchart that shows a method of specifying a reference frame and a roll-angle offset in accordance with an example embodiment that is related to the embodiment of FIG. 13.

FIG. 16 is a flowchart that shows a related method 1600 for specifying that includes operations for specifying the reference frame 1202 and the roll-angle offset 1224. A first operation 1602 includes moving the device to an initial position and orientation for the device. A second operation 1604 includes specifying the reference frame 1202 from accessed values for the device frame 1210 at the initial position and orientation for the device, the reference frame 1202 being specified to include the reference position and the reference orientation for the device. A third operation 1606 includes specifying a roll-angle offset 1224 corresponding to the initial position and orientation for the device, the device being controlled about the device roll axis to maintain the specified roll-angle offset 1224. As discussed above with reference to FIG. 14, an additional operation for specifying an RCM 112 may also be included in the method 1600.

It should be noted that, in some operational settings, the specification of the reference frame 1202 may not explicitly require the reference position (e.g., for the origin of the reference coordinate system) if that is implied or unnecessary from the context. Likewise the values for the device frame 202 may not explicitly require the device position (e.g., for the origin 204 of the frame 202) if that is implied or unnecessary from the context.

In some operational settings, the roll-control operations may be determined from pitch and yaw inputs (e.g., from a surgeon's console 600 in a teleoperated surgical system) without reference to the measured device frame. For example, input values for pitch and yaw movements from the reference orientation 1114 in FIG. 11 determine the device roll axis as the outward normal from a corresponding surface element (e.g. at second orientation 1124) of the sphere 1116. Then, this device roll axis is identified with the roll axis 1222 of the alignment frame coordinates 1220 of FIG. 12 to determine the roll-axis-alignment rotation 1218 from the reference frame 1202 to the alignment frame coordinates 1220. For example, if the pitch and yaw deviations from the reference frame define a roll-axis direction $\hat{e}_z$, then Eq. 3 is replaced by $$\left[ {}^{reference}_{alignment} R(\hat{k}, \theta) \right]_z = \hat{e}_z. \tag{4}$$

Figure 17:
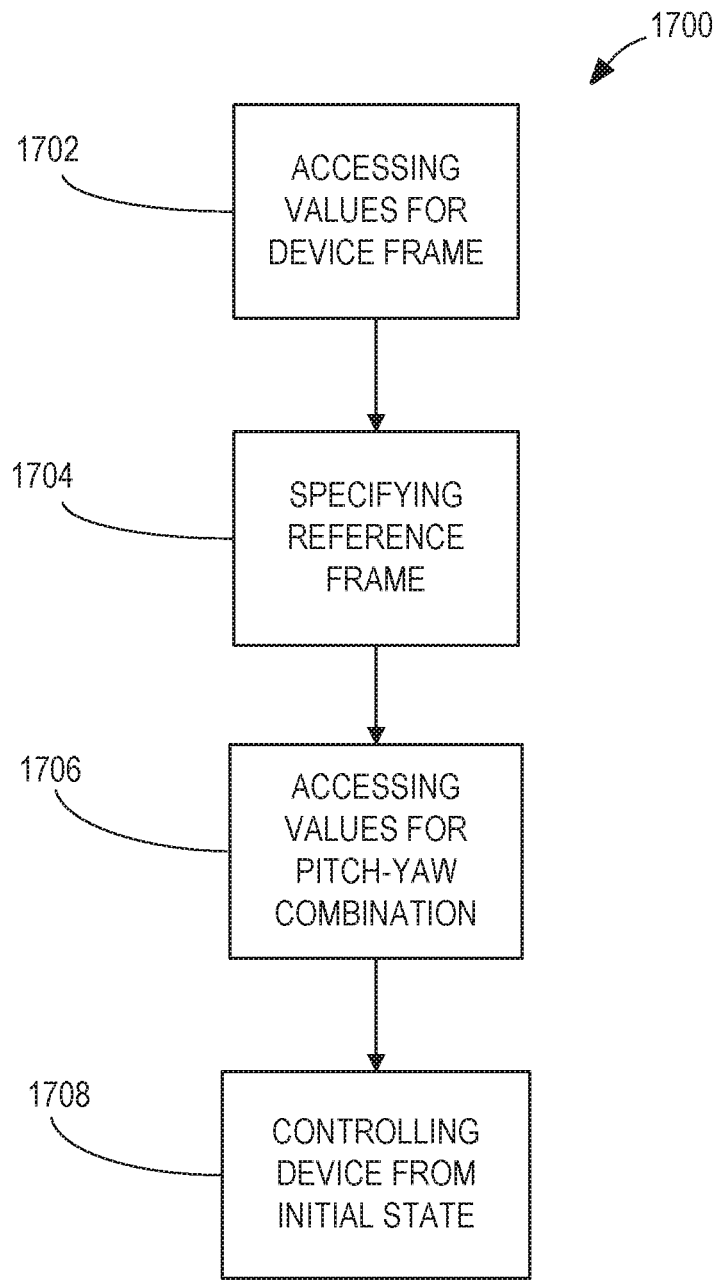
FIG. 17 is a flowchart that shows a method that includes operations based on pitch and yaw inputs for controlling a device in accordance with an example embodiment.

As discussed above, the roll-axis offset 1224 can be specified to a desired value independently of the measured device. Then the roll rotation 1226 results in a desired orientation of the device frame 1210 from the pitch and yaw inputs. FIG. 17 is a flowchart that shows a related method 1700 that includes operations based on pitch and yaw inputs for controlling a device. A first operation 1702 includes accessing values for a device frame that corresponds to an orientation of the device, the device frame including a device yaw axis, a device pitch axis, and a device roll axis. A second operation 1704 includes specifying a reference frame from the accessed values of the device frame at a reference-specifying time, the reference frame corresponding to a reference orientation for the device, and the reference frame including a reference yaw axis, a reference pitch axis, and a reference roll axis. A third operation 1706 includes accessing values for a yaw-pitch combination that includes at least one rotation about the device yaw axis and at least one rotation about the device pitch axis. A fourth operation 1708 includes controlling the device from an initial device state by implementing the pitch-yaw combination with a roll-control operation for controlling a roll-angle offset about the device roll axis, the roll-angle offset characterizing an angular difference about the device roll axis between the device frame and a roll-axis-alignment rotation of the reference frame, and the roll-axis-alignment rotation corresponding to a rotation about a combination of the reference yaw axis and the reference pitch axis to align the reference roll axis with the device roll axis.

These operations can be combined with options described above including specifying the reference frame 1202, the roll-angle offset 1224, and an RCM 112 (e.g., as in FIGS. 14 and 16).

Additional embodiments presented in FIGS. 18-21 relate to specific robotic elements for surgical applications.

Figure 18:
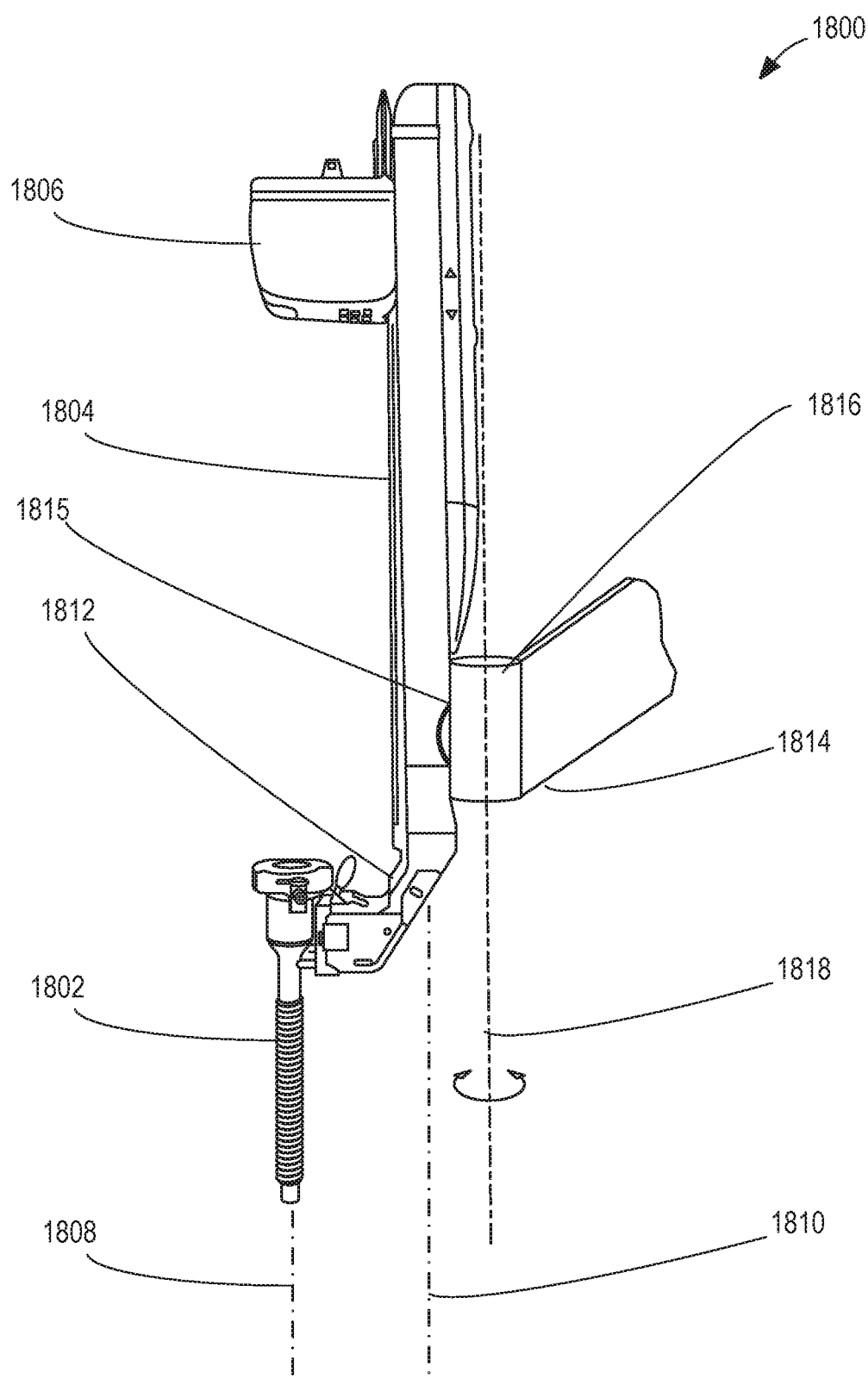
FIG. 18 is a diagram that shows a portion of a manipulator for an example embodiment related to surgical robotics.

FIG. 18 is a diagram that shows a portion of an example manipulator 1800 including a cannula 1802 mounted to a spar 1804. A surgical instrument (not shown) can be mounted to an instrument carriage 1806 attached to the spar 1804 so that the surgical instrument passes through the cannula 1802. The cannula 1802 includes a long axis 1808 that is typically parallel to, but offset from, a long axis 1810 of the spar 1804. In particular, during a surgical procedure, shafts of one or more surgical instruments pass through the cannula 1802 into the body cavity. In a teleoperated surgical system (e.g., FIGS. 6-7), a surgeon remotely controls the motion of one or more surgical instruments relative to a fixed setup structure of the manipulator 1800. This motion may include motion of the instrument shaft through control of the manipulator 1800 to which the surgical instrument is attached. In this example, the cannula 1802 is held firmly by a cannula adaptor 1812, so that it is not free floating, but instead has a fixed position relative to the spar 1804. The spar 1804 is coupled to the next proximal segment 1814 of the manipulator 1800 by a connection 1815 to a joint 1816 with an axis 1818 that is parallel to the long axis 1808 of the cannula 1802 and the long axis 1810 of the spar 1804, so that an actuation of the joint 1816 provides a roll motion for the cannula 1802 about its long axis 1808 and similarly provides a roll motion for the spar 1804 about its long axis 1810. In the example shown in FIG. 18, the long axis 1808 of the cannula 1802 is parallel to the joint axis 1816, and similarly for the spar 1804. However, other configurations are possible as discussed below.

Figure 19:
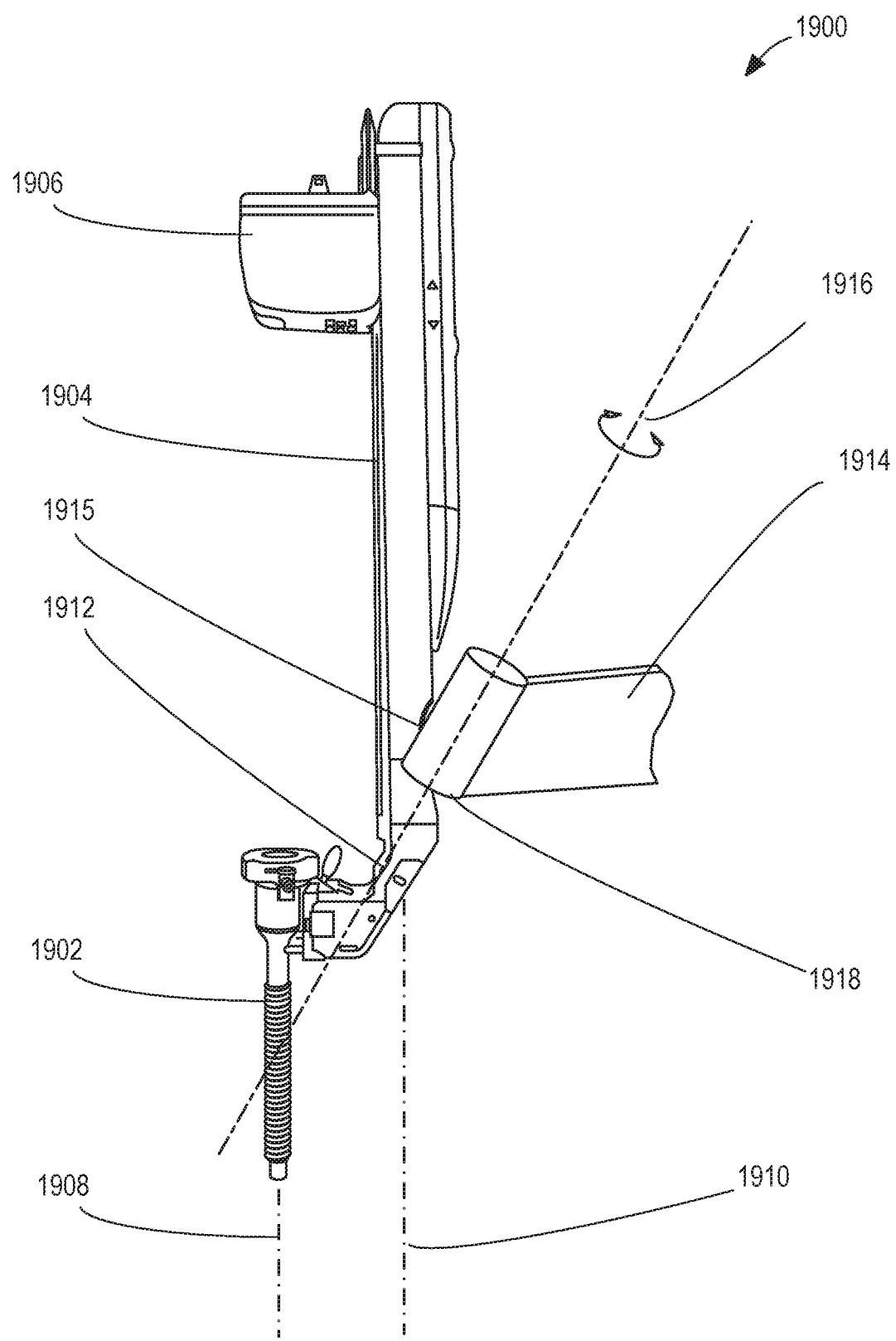
FIG. 19 is a diagram that shows a portion of a manipulator for another example embodiment related to surgical robotics.

FIG. 19 is a diagram that shows a portion of an example manipulator 1900 including a cannula 1902 mounted to a spar 1904 with an instrument carriage 1906 also attached to the spar 1904. Similarly as in FIG. 18, the cannula 1902 includes a long axis 1908 that is parallel to, but offset from, a long axis 1910 of the spar 1904, and the cannula 1902 is rigidly connected to the spar 1904 by a cannula adapter 1912. However, the spar 1904 is coupled to the next proximal segment 1914 of the manipulator 1900 by a connection 1915 to a joint 1916 with an axis 1918 that is not parallel to the long axis 1908 of the cannula 1902 or the long axis 1910 of the spar 1904, so that an actuation of the joint 1916 is insufficient to provide a roll motion for either the cannula 1902 about its long axis 1908 or the spar 1904 about its long axis 1910. To provide this long-axis roll motion for the cannula 1902 and the spar 1904, the manipulator 1900 would require a more complex combination of rotations about available joint axes (e.g., including the axis 1918).

Figure 20:
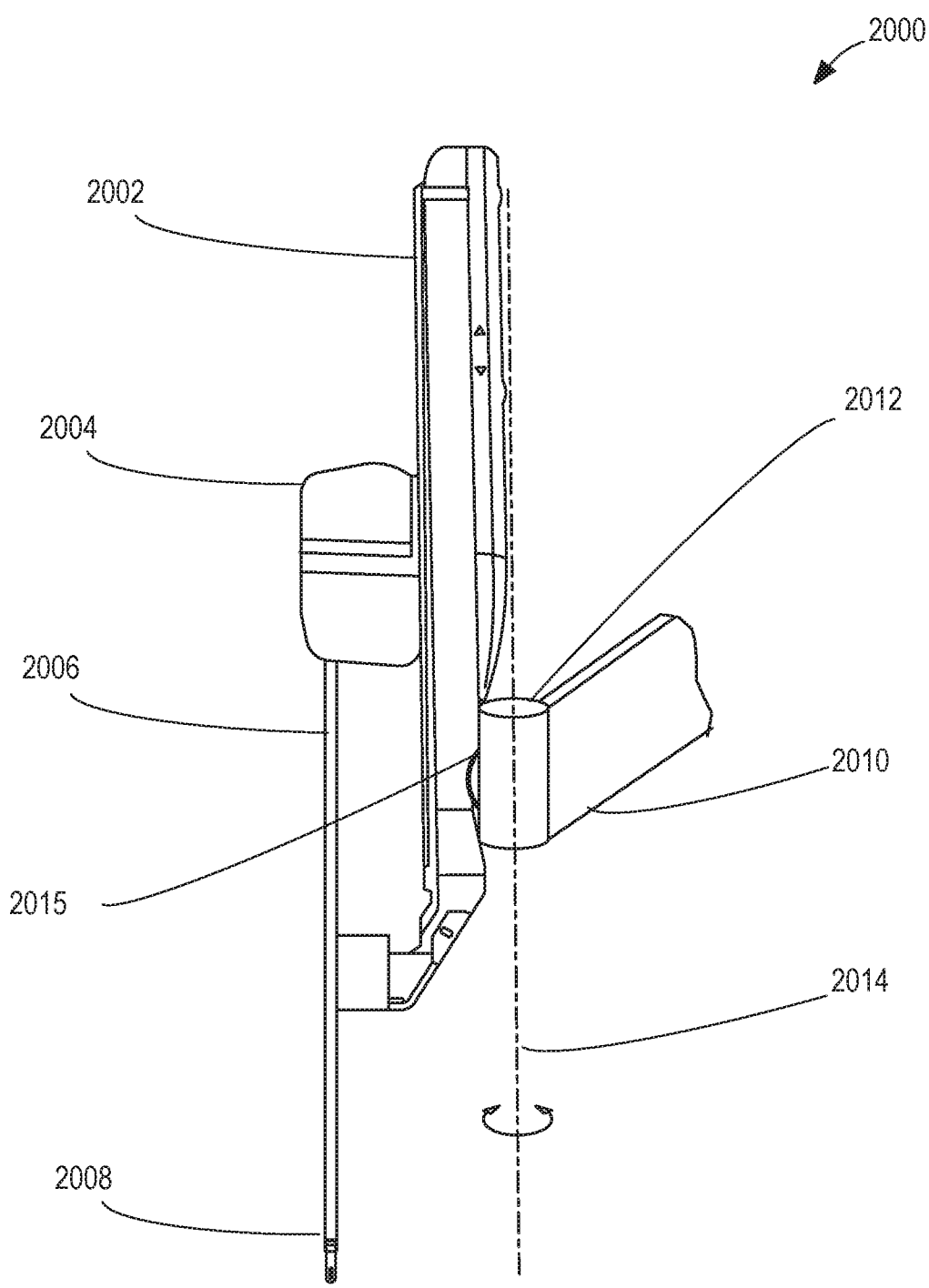
FIG. 20 is a diagram that shows a portion of a manipulator for another example embodiment related to surgical robotics.

FIG. 20 is a diagram that shows a portion of an example manipulator 2000 including a spar 2002 with an instrument carriage 2004 that supports a surgical instrument 2006 including an end effector 2008. However, in this embodiment the spar 2002 does not support a cannula as in FIGS. 18-19. The spar 2002 is coupled to the next proximal segment 2010 of the manipulator 2000 by a connection 2015 to a joint 2012 with an axis 2014 that is parallel to the long axes of the surgical instrument 2006 and the spar 2002. Similarly as in FIG. 18, an actuation of the joint 2012 provides a roll motion for the instrument 2006 about its long axis and similarly provides a roll motion for the spar 2002 about its long axis.

Figure 21:
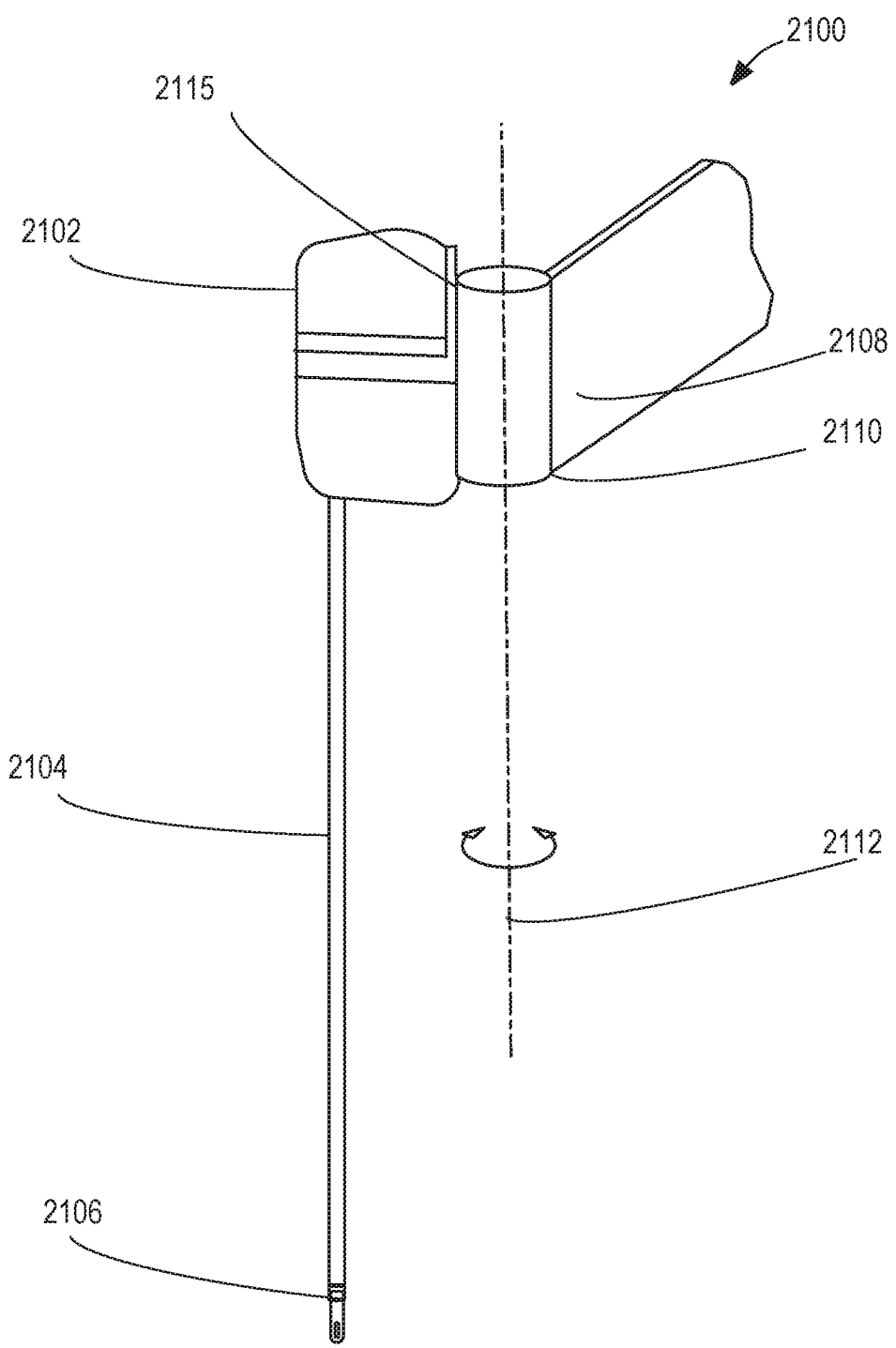
FIG. 21 is a diagram that shows a portion of a manipulator for another example embodiment related to surgical robotics.

FIG. 21 is a diagram that shows a portion of an example manipulator 2100 that includes neither a spar nor a cannula. An instrument carriage 2102 supports a surgical instrument 2104 that includes an end effector 2106. The instrument carriage 2102 is coupled to the next proximal segment 2108 of the manipulator 2100 by a connection 2115 to a joint 2110 with an axis 2112 that is parallel to the long axis of the surgical instrument 2104. Similarly as in FIG. 20, an actuation of the joint 2110 provides a roll motion for the instrument 2104 about its long axis.

Additional embodiments correspond to systems and related computer programs that carry out the above-described methods.

Figure 22:
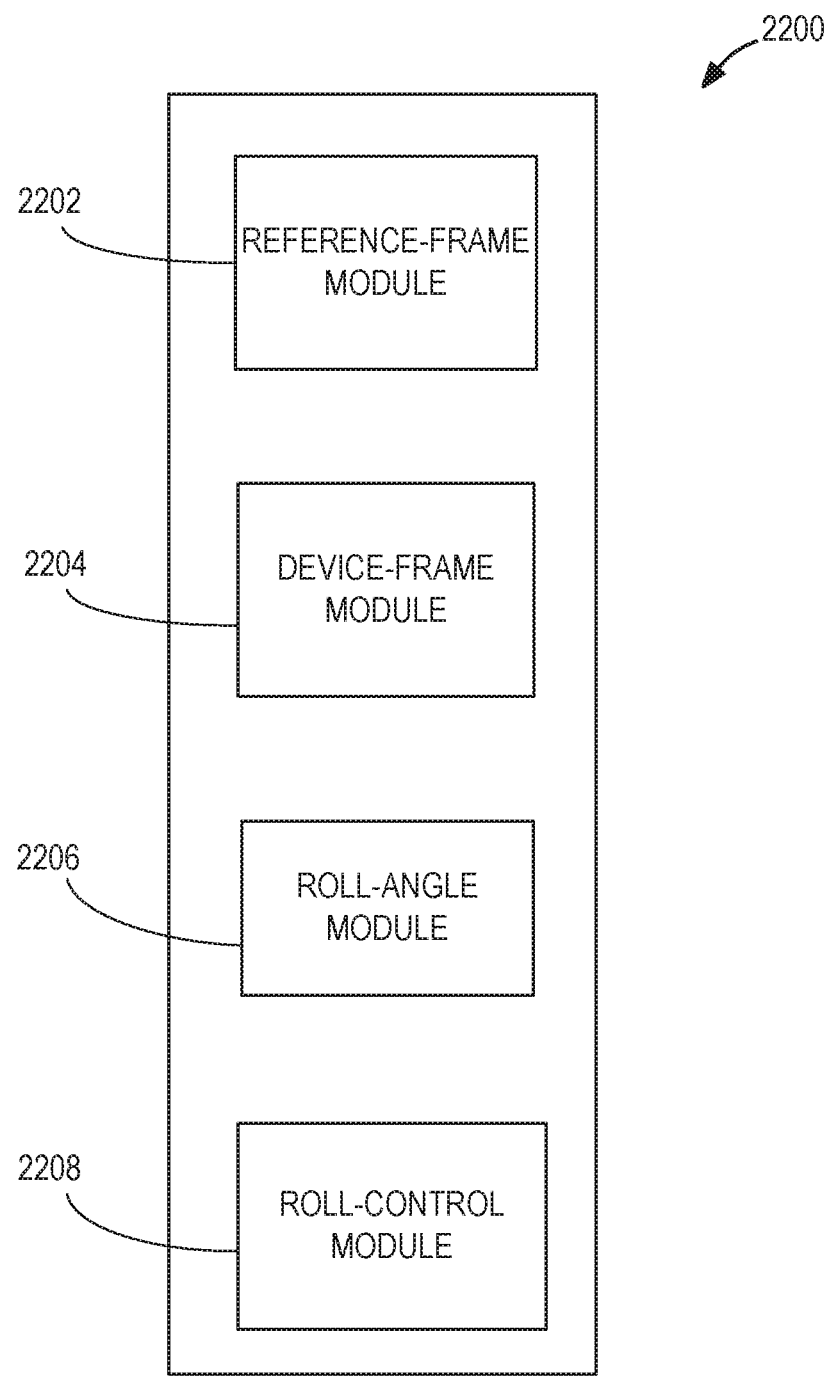
FIG. 22 is a block diagram that shows a schematic representation of an apparatus for an example embodiment related to the embodiment of FIG. 13.

FIG. 22 shows a schematic representation of an apparatus 2200, in accordance with an example embodiment for controlling roll for a device. In this case, the apparatus 2200 includes at least one computer system (e.g., as in FIG. 24) that is configured to perform software and hardware operations for modules that carry out aspects of the method 1300 of FIG. 13.

In this example embodiment, the apparatus 2200 includes a reference-frame module 2202, a device-frame module 2204, a roll-angle module 2206, and a roll-control module 2208. The reference-frame module 2202 operates to specify a reference frame 1202 that corresponds to a reference orientation 1010 for the device, where the reference frame 1202 includes a reference yaw axis 1204, a reference pitch axis 1206, and a reference roll axis 1208. The device-frame module 2204 operates to access values for a device frame 1202 that corresponds to an orientation of the device, where the device frame 1210 includes a device yaw axis 1214, a device pitch axis 1212, and a device roll axis 1216.

The roll-angle module 2206 operates to determine a roll-angle offset that characterizes an angular difference about the device roll axis 1216 between the device frame 1210 and a roll-axis-alignment rotation of the reference frame 1202, where the roll-axis-alignment rotation corresponds to a rotation about a combination of the reference yaw axis 1204 and the reference pitch axis 1206 to align the reference roll axis 1208 with the device roll axis 1216. The roll-control module 2208 operates to control roll for the device by rotating the device by an amount corresponding to the roll-angle offset about the device roll axis 1216. Additional operations related to the method 1300 may be performed by additional corresponding modules or through modifications of the above-described modules.

Figure 23:
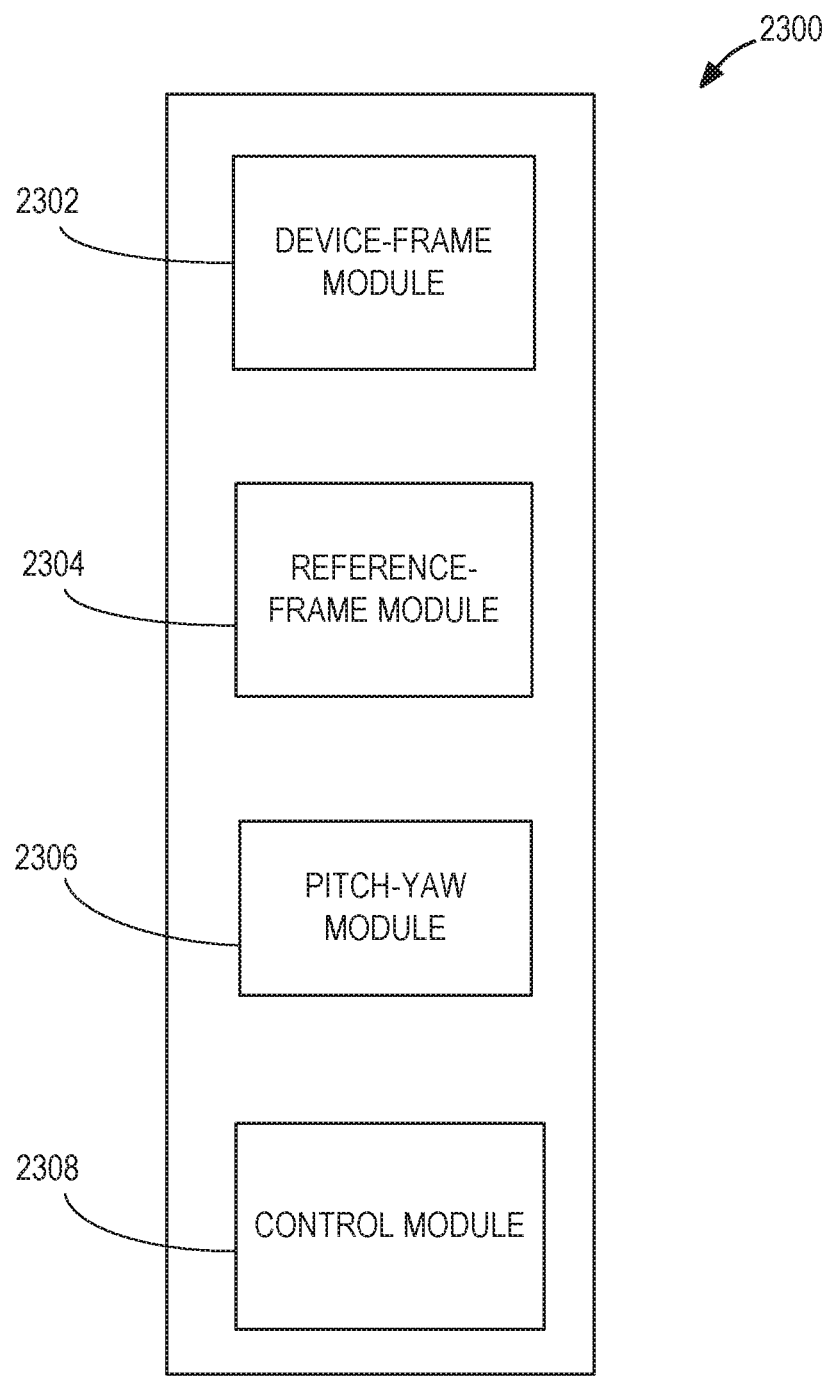
FIG. 23 is a block diagram that shows a schematic representation of an apparatus for an example embodiment related to the embodiment of FIG. 17.

FIG. 23 shows a schematic representation of an apparatus 2300, in accordance with an example embodiment for controlling roll for a device. In this case, the apparatus 2300 includes at least one computer system (e.g., as in FIG. 20) that is configured to perform software and hardware operations for modules that carry out aspects of the method 1700 of FIG. 17.

In this example embodiment, the apparatus 2300 includes a frame-access module 2302, a reference-frame module 2204, a pitch-yaw module 2306, and a control module 2208. The frame-access module 2302 operates to access values for a device frame that corresponds to an orientation of the device, the device frame including a device yaw axis, a device pitch axis, and a device roll axis. The reference-frame module 2204 operates to specify a reference frame from the accessed values of the device frame at a reference-specifying time, the reference frame corresponding to a reference orientation for the device, and the reference frame including a reference yaw axis, a reference pitch axis, and a reference roll axis.

Figure 24:
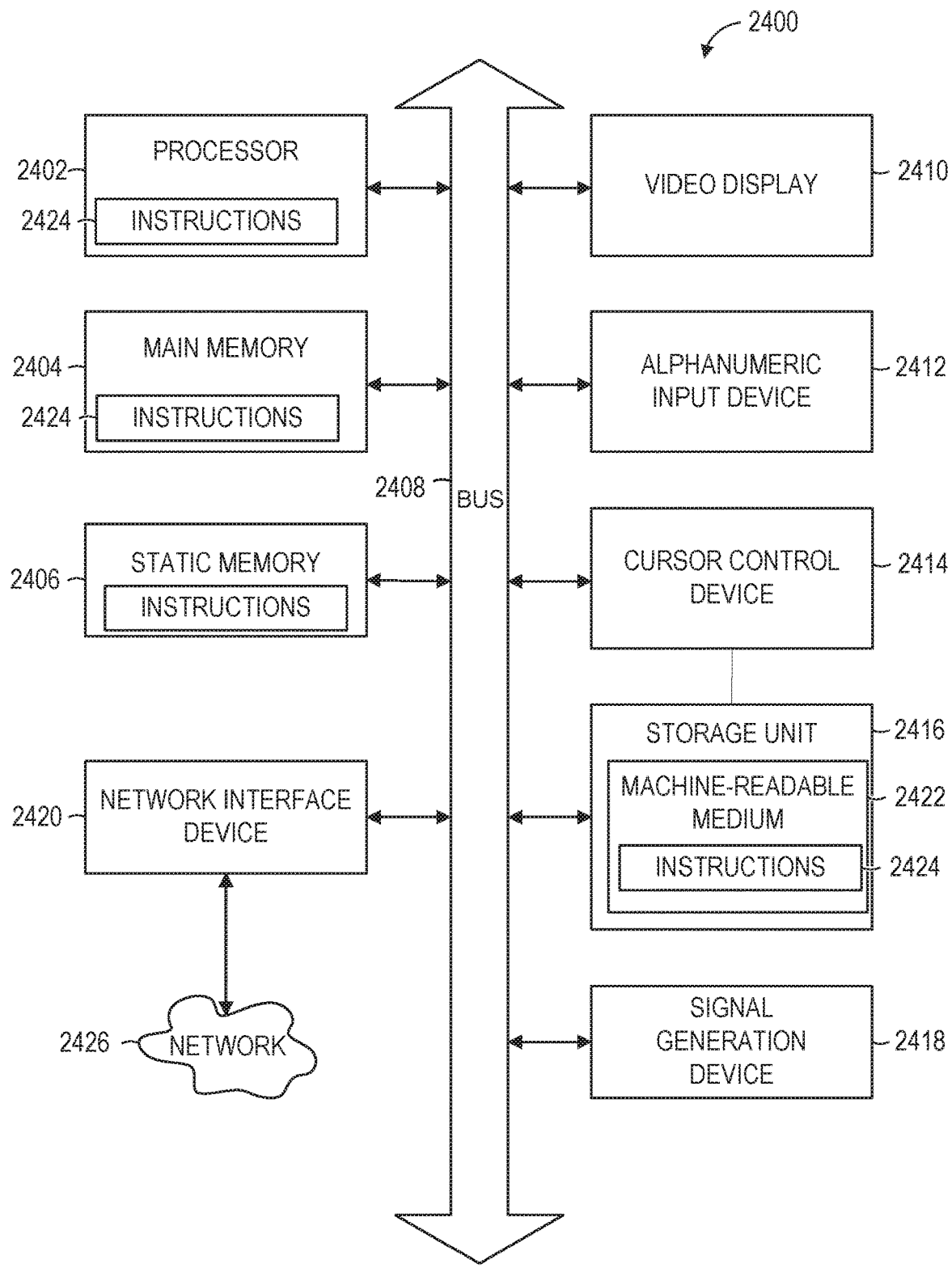
FIG. 24 is a block diagram of a computer system within which a set of instructions for causing the computer to perform any one of the methodologies discussed herein may be executed.

The pitch-yaw module 2306 operates to access values for a yaw-pitch combination that includes at least one rotation about the device yaw axis and at least one rotation about the device pitch axis. The control module 2208 operates to control the device from an initial device state by implementing the pitch-yaw combination with a roll-control operation for controlling a roll-angle offset about the device roll axis, the roll-angle offset characterizing an angular difference about the device roll axis between the device frame and a roll-axis-alignment rotation of the reference frame, and the roll-axis-alignment rotation corresponding to a rotation about a combination of the reference yaw axis and the reference pitch axis to align the reference roll axis with the device roll axis FIG. 24 shows a machine in the example form of a computer system 2400 within which instructions for causing the machine to perform any one or more of the methodologies discussed here may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 2400 includes a processor 2402 (e.g., a central processing unit (CPU), a graphics processing unit (GPU) or both), a main memory 2404, and a static memory 2406, which communicate with each other via a bus 2408. The computer system 2400 may further include a video display unit 2410 (e.g., a liquid crystal display (LCD) or a cathode ray tube (CRT)). The computer system 2400 also includes an alphanumeric input device 2412 (e.g., a keyboard), a user interface (UI) cursor control device 2414 (e.g., a mouse), a storage unit 2416 (e.g., a disk drive), a signal generation device 2418 (e.g., a speaker), and a network interface device 2420.

In some contexts, a computer-readable medium may be described as a machine-readable medium. The storage unit 2416 includes a machine-readable medium 2422 on which is stored one or more sets of data structures and instructions 2424 (e.g., software) embodying or utilizing any one or more of the methodologies or functions described herein. The instructions 2424 may also reside, completely or at least partially, within the static memory 2406, within the main memory 2404, or within the processor 2402 during execution thereof by the computer system 2400, with the static memory 2406, the main memory 2404, and the processor 2402 also constituting machine-readable media.

While the machine-readable medium 2422 is shown in an example embodiment to be a single medium, the terms "machine-readable medium" and "computer-readable medium" may each refer to a single storage medium or multiple storage media (e.g., a centralized or distributed database, and/or associated caches and servers) that store the one or more sets of data structures and instructions 2424. These terms shall also be taken to include any tangible or non-transitory medium that is capable of storing, encoding or carrying instructions for execution by the machine and that cause the machine to perform any one or more of the methodologies disclosed herein, or that is capable of storing, encoding or carrying data structures utilized by or associated with such instructions. These terms shall accordingly be taken to include, but not be limited to, solid-state memories, optical media, and magnetic media. Specific examples of machine-readable or computer-readable media include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; compact disc read-only memory (CD-ROM) and digital versatile disc read-only memory (DVD-ROM). However, the terms "machine-readable medium" and "computer-readable medium" are intended to specifically exclude non-statutory signals per se.

The instructions 2424 may further be transmitted or received over a communications network 2426 using a transmission medium. The instructions 2424 may be transmitted using the network interface device 2420 and any one of a number of well-known transfer protocols (e.g., hypertext transfer protocol (HTTP)). Examples of communication networks include a local area network (LAN), a wide area network (WAN), the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Certain embodiments are described herein as including logic or a number of components, modules, or mechanisms. Modules may constitute either software modules or hardware-implemented modules. A hardware-implemented module is a tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module (e.g., a computer-implemented module) may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" (e.g., a "computer-implemented module") should be understood to encompass a tangible entity, be that an entity that is physically constructed, permanently configured (e.g., hardwired), or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation and store the output of that operation in a memory device to which it is communicatively coupled. A further hardware-implemented module may then, at a later time, access the memory device to retrieve and process the stored output. Hardware-implemented modules may also initiate communications with input or output devices and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

Although only certain embodiments have been described in detail above, those skilled in the art will readily appreciate that many modifications are possible without materially departing from the novel teachings of this disclosure. For example, aspects of embodiments disclosed above can be combined in other combinations to form additional embodiments. Accordingly, all such modifications are intended to be included within the scope of this disclosure.

What is claimed is:

1. A method of controlling roll for a device in a computer-assisted medical system, the method comprising:
    specifying a reference frame that corresponds to a reference orientation for the device, the reference frame including a reference yaw axis, a reference pitch axis, and a reference roll axis;
    accessing values for a device frame that corresponds to an orientation of the device, the device frame including a device yaw axis, a device pitch axis, and a device roll axis;
    determining a roll-angle offset about the device roll axis, the roll-angle offset characterizing an angular difference about the device roll axis between the device frame and a roll-axis-alignment rotation of the reference frame, and the roll-axis-alignment rotation corresponding to a rotation about a combination of the reference yaw axis and the reference pitch axis to align the reference roll axis with the device roll axis; and
    controlling roll for the device by controlling the roll-angle offset about the device roll axis.

2. The method of claim 1, wherein controlling the roll-angle offset includes rotating the device about the device roll axis to maintain a specified roll-angle offset.

3. The method of claim 1, wherein controlling the roll-angle offset includes rotating the device about the device roll axis by an amount based on a comparison between the determined roll-angle offset at a given time and a specified roll-angle offset.

4. The method of claim 1, further comprising:
    specifying a remote center of motion (RCM) at a given location of the device, the RCM corresponding to an origin of the device frame; and maintaining the RCM at a given location in the reference frame while controlling roll for the device by controlling the roll-angle offset about the device roll axis.

5. The method of claim 1, further comprising:
determining a first orientation of the device from the accessed values for the device frame at a first time, the first orientation corresponding to a first roll-angle offset about the device roll axis;
specifying a second orientation corresponding to a second roll-angle offset about the device roll axis; and
controlling the device from the first orientation to the second orientation by controlling the roll-angle offset about the device roll axis from the first roll-angle offset to the second roll-angle offset in combination with operations for controlling the device about the device pitch axis and device roll axis from the first orientation to the second orientation.

6. The method of claim 1, wherein the reference frame is a first reference frame that corresponds to a first position and orientation for the device, and the method further comprises:
disengaging the control of the roll-angle offset with respect to the first reference frame at a first time;
after a movement of the device to a second position and orientation for the device at a second time that is after the first time,
specifying a second reference frame from accessed values for the device frame at the second position and orientation for the device; and
controlling the roll-angle offset with respect to the second reference frame at a third time that is after the second time.

7. A computer-assisted medical system comprising at least one computer configured to perform operations for computer-implemented modules including:
a reference-frame module configured to specify a reference frame that corresponds to a reference orientation for a device, the reference frame including a reference yaw axis, a reference pitch axis, and a reference roll axis;
a device-frame module configured to access values for a device frame that corresponds to an orientation of the device, the device frame including a device yaw axis, a device pitch axis, and a device roll axis;
a roll-angle module configured to determine a roll-angle offset about the device roll axis, the roll-angle offset characterizing an angular difference about the device roll axis between the device frame and a roll-axis-alignment rotation of the reference frame, and the roll-axis-alignment rotation corresponding to a rotation about a combination of the reference yaw axis and the reference pitch axis to align the reference roll axis with the device roll axis; and
a roll-control module configured to control roll for the device by controlling the roll-angle offset about the device roll axis.

8. The system of claim 7, wherein controlling the roll-angle offset includes rotating the device about the device roll axis to maintain a specified roll-angle offset.

9. The system of claim 7, wherein controlling the roll-angle offset includes rotating the device about the device roll axis by an amount corresponding to a difference between the determined roll-angle offset at a given time and a specified roll-angle offset.

10. The system of claim 7, wherein controlling the roll-angle offset includes rotating the device about the device roll axis by an amount based on a comparison between the determined roll-angle offset at a given time and a specified roll-angle offset.

11. The system of claim 7, wherein:
a difference between the device frame and the reference frame includes a yaw-angle offset relative to the reference yaw axis and a pitch-angle offset relative to the reference pitch axis; and
the roll-axis-alignment rotation corresponds to a rotation for the yaw-angle offset about the reference yaw axis, a rotation for the pitch-angle offset about the reference pitch axis, and no rotation about the reference roll axis.

12. The system of claim 7, wherein the roll-control module is further configured to perform operations comprising:
specifying a remote center of motion (RCM) at a given location of the device, the RCM corresponding to an origin of the device frame; and
maintaining the RCM at a given location in the reference frame while controlling roll for the device by controlling the roll-angle offset about the device roll axis.

13. The system of claim 7, wherein the roll-control module is further configured to perform operations comprising:
determining a first orientation of the device from the accessed values for the device frame at a first time, the first orientation corresponding to a first roll-angle offset about the device roll axis;
specifying a second orientation corresponding to a second roll-angle offset about the device roll axis; and
controlling the device from the first orientation the second orientation by controlling the roll-angle offset about the device roll axis from the first roll-angle offset to the second roll-angle offset in combination with operations for controlling the device about the device pitch axis and device roll axis from the first orientation to the second orientation.

14. The system of claim 7, wherein the roll-control module is further configured to perform operations comprising:
accessing values for the device frame at an initial position and orientation for the device;
specifying the reference frame from the accessed values for the device frame at the initial position and orientation for the device, the reference frame being specified to include athc reference position and the reference orientation for the device; and
specifying a roll-angle offset corresponding to the initial position and orientation for the device, the device being controlled about the device roll axis to maintain the specified roll-angle offset.

15. The system of claim 7, wherein the reference frame is a first reference frame that corresponds to a first position and orientation for the device, and the roll-control module is further configured to perform operations comprising:
disengaging the control of the roll-angle offset with respect to the first reference frame at a first time;
accessing values for the device frame at a second position and orientation for the device at a second time that is after the first time;
specifying a second reference frame from the accessed values for the device frame at the second position and orientation for the device; and
controlling the roll-angle offset with respect to the second reference frame at a third time that is after the second time.

16. The system of claim 7, wherein:
controlling roll for the device includes transmitting at least one command to at least one actuator for rotating the device about the device roll axis; and
wherein the device is a medical device that includes a spar for mounting a surgical tool, the spar having a long axis that corresponds to the device roll axis.

17. The system of claim 7, wherein the roll-angle offset is controlled independently of control for pitch about the device pitch axis and yaw about the device yaw axis.

18. A computer-readable medium that stores a computer program for controlling roll for a device in a computer-assisted medical system, the computer program including computer-program instructions that, when executed by at least one computer, cause the at least one computer to perform operations comprising:
specifying a reference frame that corresponds to a reference orientation for the device, the reference frame including a reference yaw axis, a reference pitch axis, and a reference roll axis;
accessing values for a device frame that corresponds to an orientation of the device, the device frame including a device yaw axis, a device pitch axis, and a device roll axis;
determining a roll-angle offset about the device roll axis, the roll-angle offset characterizing an angular difference about the device roll axis between the device frame and a roll-axis-alignment rotation of the reference frame, and the roll-axis-alignment rotation corresponding to a rotation about a combination of the reference yaw axis and the reference pitch axis to align the reference roll axis with the device roll axis; and
controlling roll for the device by controlling the roll-angle offset about the device roll axis.

19. The computer-readable medium of claim 18, wherein controlling the roll-angle offset includes:
rotating the device about the device roll axis to maintain a specified roll-angle offset; or
rotating the device about the device roll axis by an amount corresponding to a difference between the determined roll-angle offset at a given time and a specified roll-angle offset; or
rotating the device about the device roll axis by an amount based on a comparison between the determined roll-angle offset at a given time and a specified roll-angle offset.

20. The computer-readable medium of claim 18, wherein the operations further comprise:
specifying a remote center of motion (RCM) at a given location of the device, the RCM corresponding to an origin of the device frame; and
maintaining the RCM at a given location in the reference frame while controlling roll for the device by controlling the roll-angle offset about the device roll axis.

* * * * *

UNITED STATES PATENT AND TRADEMARK OFFICE
CERTIFICATE OF CORRECTION

PATENT NO. : 10,758,313 B2
APPLICATION NO. : 15/766778
DATED : September 1, 2020
INVENTOR(S) : Nicholas Bernstein Page 1 of 1

It is certified that error appears in the above-identified patent and that said Letters Patent is hereby corrected as shown below:

In the Claims

Claim 14, Column 20, Line 46, "athc", should read the word -- a --.

Signed and Sealed this
Twenty-seventh Day of October, 2020

Andrei Iancu
*Director of the United States Patent and Trademark Office*